(12) United States Patent
Park et al.

(10) Patent No.: US 11,133,469 B2
(45) Date of Patent: Sep. 28, 2021

(54) COMPOUNDS FOR ORGANIC OPTOELECTRONIC DEVICE AND ORGANIC OPTOELECTRONIC DEVICE INCLUDING THE SAME

(71) Applicant: UNIVERSITY-INDUSTRY COOPERATION GROUP OF KYUNG HEE UNIVERSITY, Yongin-si (KR)

(72) Inventors: Jong Wook Park, Seoul (KR); Hayoon Lee, Incheon (KR)

(73) Assignee: UNIVERSITY-INDUSTRY COOPERATION GROUP OF KYUNG HEE UNIVERSITY, Yongin-si (KR)

( * ) Notice: Subject to any disclaimer, the term of this patent is extended or adjusted under 35 U.S.C. 154(b) by 520 days.

(21) Appl. No.: 15/642,520

(22) Filed: Jul. 6, 2017

(65) Prior Publication Data
US 2018/0019403 A1  Jan. 18, 2018

(30) Foreign Application Priority Data
Jul. 12, 2016 (KR) .................. 10-2016-0088213

(51) Int. Cl.
| | | |
|---|---|---|
| H01L 51/54 | (2006.01) | |
| H01L 51/00 | (2006.01) | |
| C07D 209/86 | (2006.01) | |
| C07C 211/54 | (2006.01) | |
| C07D 251/24 | (2006.01) | |
| C07C 211/61 | (2006.01) | |
| C07C 13/72 | (2006.01) | |
| C09K 11/02 | (2006.01) | |
| C09K 11/06 | (2006.01) | |

(Continued)

(52) U.S. Cl.
CPC .......... *H01L 51/0058* (2013.01); *C07C 13/72* (2013.01); *C07C 211/54* (2013.01); *C07C 211/61* (2013.01); *C07D 209/86* (2013.01); *C07D 251/24* (2013.01); *C09K 11/025* (2013.01); *C09K 11/06* (2013.01); *H01L 51/006* (2013.01); *H01L 51/0056* (2013.01); *H01L 51/0059* (2013.01); *H01L 51/0067* (2013.01); *H01L 51/0072* (2013.01); *C09K 2211/1011* (2013.01); *H01L 51/42* (2013.01); *H01L 51/5012* (2013.01); *H01L 51/5016* (2013.01); *H01L 51/5064* (2013.01)

(58) Field of Classification Search
CPC ....... C07C 13/72; C07C 13/62; C07C 211/54; C07C 211/61; C09K 11/025; C09K 11/06; C09K 2211/1011; H01L 51/0058; H01L 51/5012; H01L 51/5016; H01L 51/0059; H01L 51/006; H01L 51/0056

USPC .............. 428/690, 691, 917; 427/58, 66; 313/500–512; 257/40, 88–104, 257/E51.001–E51.052; 252/301.16–301.35

See application file for complete search history.

(56) References Cited

U.S. PATENT DOCUMENTS 8,815,417 B2   8/2014 Kim

FOREIGN PATENT DOCUMENTS

| KR | 10-2010-0112903 | 10/2010 |
| KR | 20100112903 A * | 10/2010 |

(Continued)

OTHER PUBLICATIONS

Han et al., machine translation of KR 2010-0112903 (2010) pp. 1-42. (Year: 2010).*

(Continued)

*Primary Examiner* — Dylan C Kershner
(74) *Attorney, Agent, or Firm* — Lex IP Meister, PLLC

(57) ABSTRACT

A compound for an organic optoelectronic device represented by Chemical Formula 1 and an organic optoelectronic device including the same are provided.

[Chemical Formula 1]

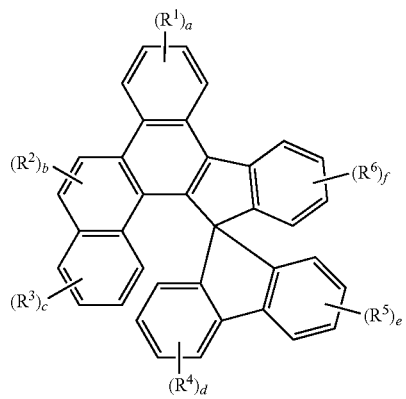

In Chemical Formula 1,
R1 to R5 are independently hydrogen, deuterium, —NH2, a substituted or unsubstituted C1 to C30 alkylamine group, a substituted or unsubstituted C26 to C30 arylamine group, a substituted or unsubstituted C1 to C30 alkyl group, a substituted or unsubstituted C6 to C30 aryl group, a substituted or unsubstituted C2 to C30 heteroaryl group, or a combination thereof,
at least one of R2, R4, and R5 is a substituted or unsubstituted C6 to C30 aryl group, a substituted or unsubstituted C6 to C30 arylamine group, or a substituted or unsubstituted C2 to C30 heteroaryl group, (Continued)

each of a, c, d, e, and f is an integer of 1 to 4, and b is an integer of 1 or 2.

3 Claims, 9 Drawing Sheets

(51) Int. Cl.
    *H01L 51/50*     (2006.01)
    *H01L 51/42*     (2006.01)

(56) References Cited

FOREIGN PATENT DOCUMENTS

| | | |
|---|---|---|
| KR | 10-2014-0119438 | 10/2014 |
| KR | 10-2017-0057017 | 5/2017 |
| WO | 2014-163305 | 10/2014 |
| WO | WO-2014163305 A1 * | 10/2014 |

OTHER PUBLICATIONS

Lee et al., machine translation of WO 2014-163305 (2014) pp. 1-19. (Year: 2014).*

* cited by examiner

COMPOUNDS FOR ORGANIC OPTOELECTRONIC DEVICE AND ORGANIC OPTOELECTRONIC DEVICE INCLUDING THE SAME

CROSS-REFERENCE TO RELATED APPLICATION

This application claims priority to and the benefit of Korean Patent Application No. 10-2016-0088213 filed in the Korean Intellectual Property Office on Jul. 12, 2016, the entire contents of which are incorporated herein by reference.

BACKGROUND OF THE INVENTION

(a) Field of the Invention

A compound for an organic optoelectronic device and an organic optoelectronic device including the same are disclosed.

(b) Description of the Related Art

An organic optoelectronic device is a device that converts electrical energy into photoenergy, and vice versa.

An organic optoelectronic device may be classified as follows in accordance with its driving principles. One is a photoelectric device where excitons are generated by photoenergy, separated into electrons and holes, and transferred to different electrodes to generate electrical energy, and the other is a light emitting device where a voltage or a current is supplied to an electrode to generate photoenergy from electrical energy.

Examples of an organic optoelectronic device may be an organic photoelectric device, an organic light emitting diode, and an organic solar cell.

Of these, the organic light emitting diode (OLED) has recently drawn attention due to an increase in demand for flat panel displays. The organic light emitting diode is a device that converts electrical energy into light by applying current to an organic light emitting material, and has a structure in which an organic layer is disposed between an anode and a cathode. A light emitting wavelength and performance of an organic light emitting diode may be affected by characteristics of the organic layer, and among them, may be mainly affected by characteristics of an organic material of the organic layer.

SUMMARY OF THE INVENTION

An embodiment provides a compound applicable to an organic optoelectronic device.

Another embodiment provides an organic optoelectronic device including the compound.

According to an embodiment, a compound for an organic optoelectronic device represented by Chemical Formula 1 is provided.

[Chemical Formula 1]

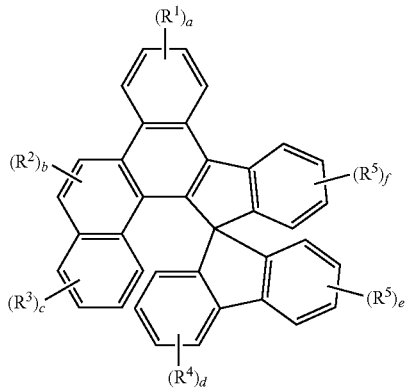

In Chemical Formula 1, $R^1$ to $R^5$ are independently hydrogen, deuterium, $-NH_2$, a substituted or unsubstituted C1 to C30 alkylamine group, a substituted or unsubstituted C6 to C30 arylamine group, a substituted or unsubstituted C1 to C30 alkyl group, a substituted or unsubstituted C6 to C30 aryl group, a substituted or unsubstituted C2 to C30 heteroaryl group, or a combination thereof, at least one of $R^2$, $R^4$, and $R^5$ is a substituted or unsubstituted C6 to C30 aryl group, a substituted or unsubstituted C6 to C30 arylamine group, or a substituted or unsubstituted C2 to C30 heteroaryl group, each of a, c, d, e, and f is an integer of 1 to 4, and b is an integer of 1 or 2.

In Chemical Formula 1, at least one $R^4$ and at least one $R^5$ may be the same or different, and may be selected from a substituted or unsubstituted C6 to C30 aryl group, a substituted or unsubstituted C6 to C30 arylamine group, a substituted or unsubstituted C2 to C30 heteroaryl group, and a combination thereof.

In Chemical Formula 1, at least one $R^4$ and at least one $R^5$ may be selected from a substituted or unsubstituted C6 to C30 aryl group, a substituted or unsubstituted C6 to C30 arylamine group, a substituted or unsubstituted C2 to C30 heteroaryl group, and a combination thereof.

In Chemical Formula 1, at least one $R^2$ and at least one $R^5$ may be selected from a substituted or unsubstituted C6 to C30 aryl group, a substituted or unsubstituted C6 to C30 arylamine group, a substituted or unsubstituted C2 to C30 heteroaryl group, and a combination thereof.

Specific examples of the compound represented by Chemical Formula 1 may be compounds of Chemical Formulae A-1 to E-15.

[A-1]
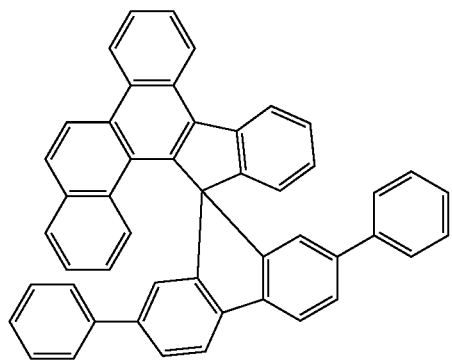
[A-2]
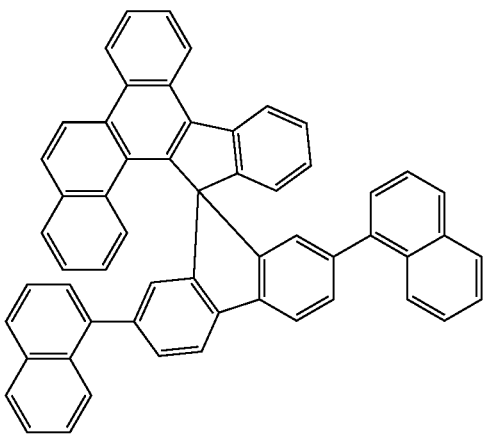
[A-3]
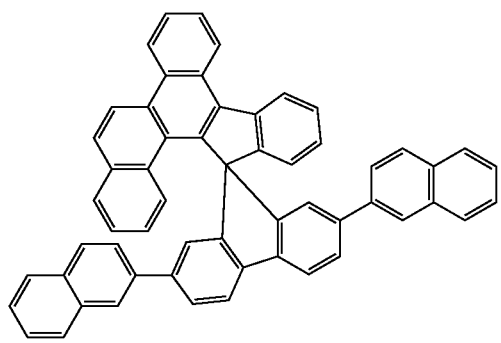
[A-4]
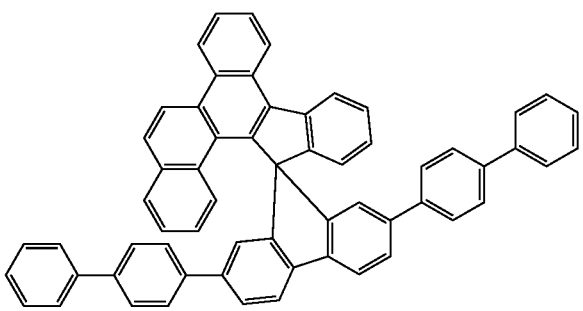
[A-5]
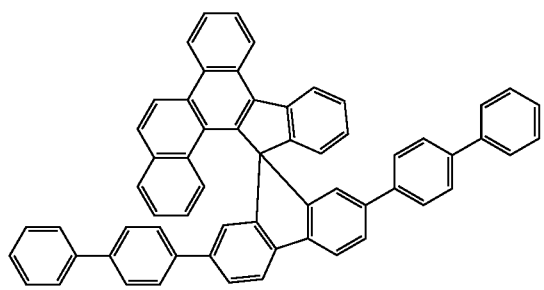
[A-6]
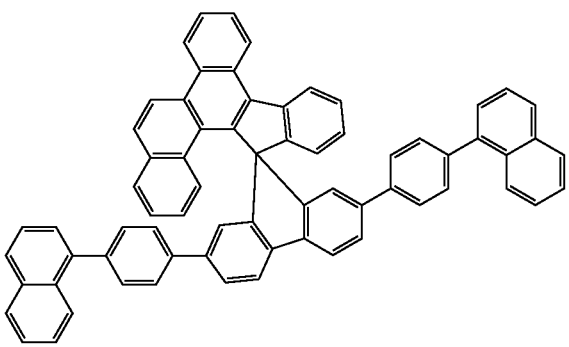
[A-7]
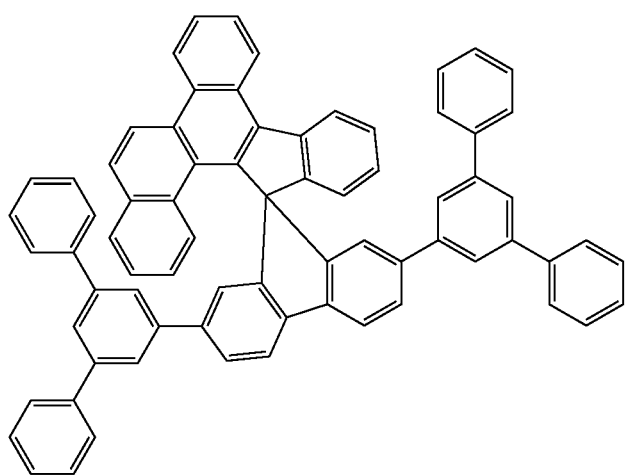

[A-8]
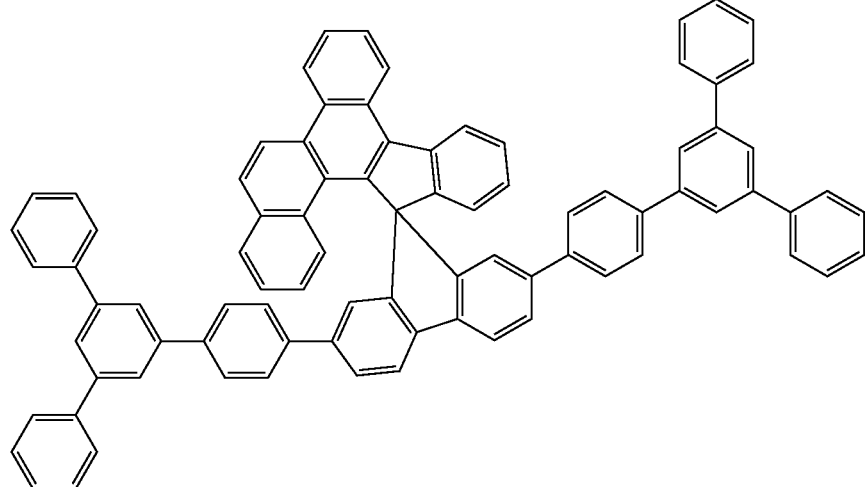
[A-9]
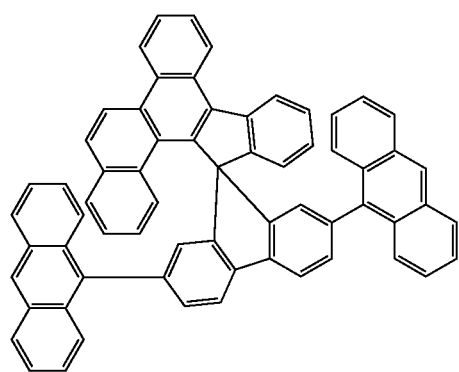
[A-10]
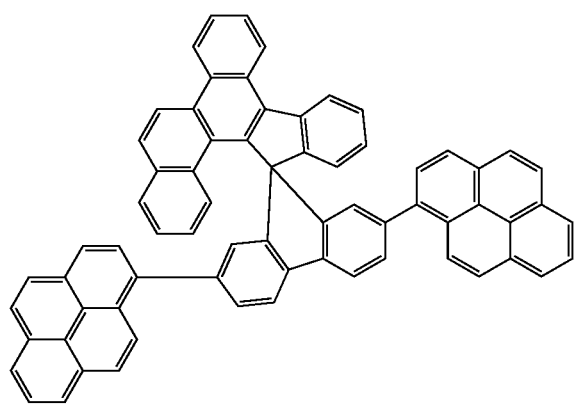
[B-1]
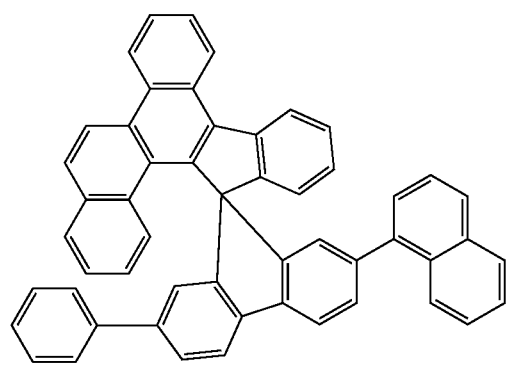
[B-2]
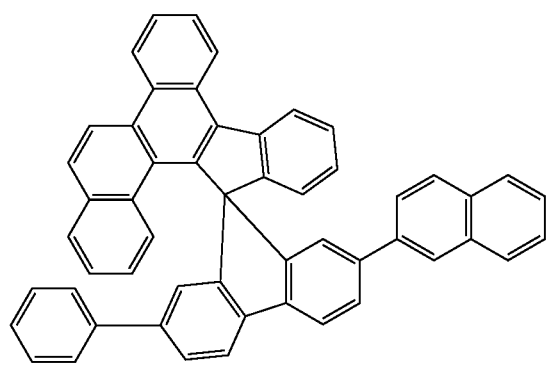

-continued
[B-3]
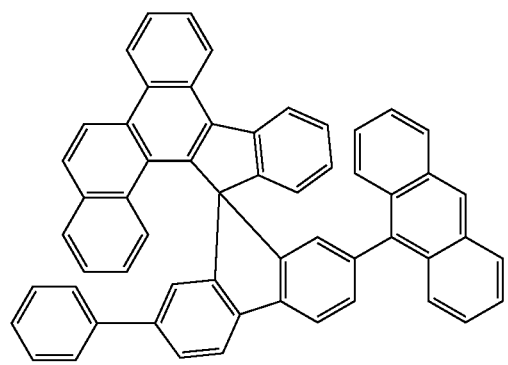
[B-4]
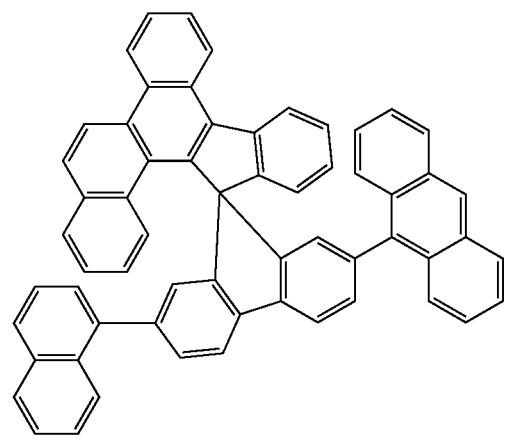
[B-5]
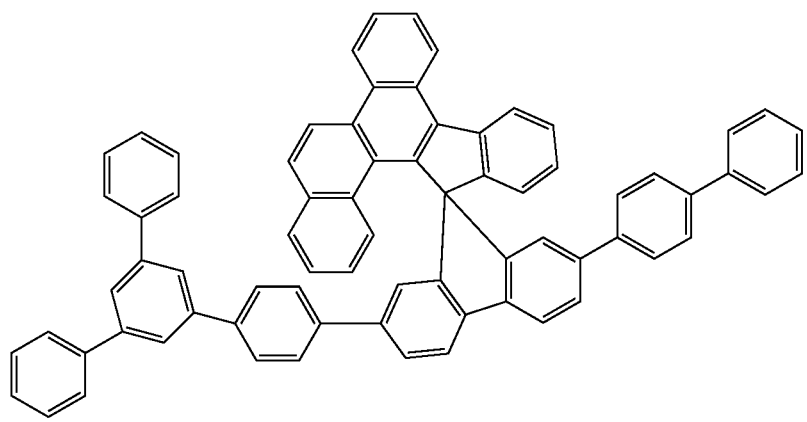
[C-1]
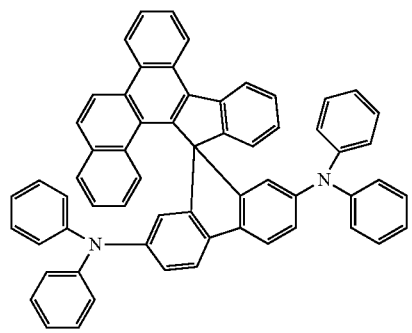
[C-2]
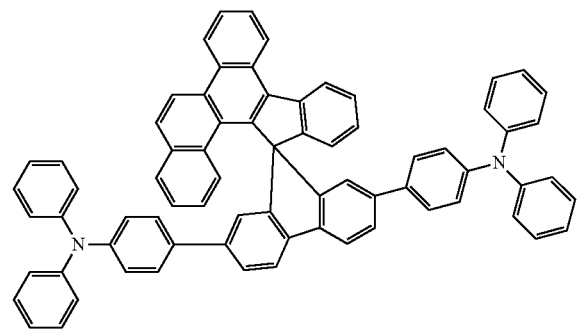
[C-3]
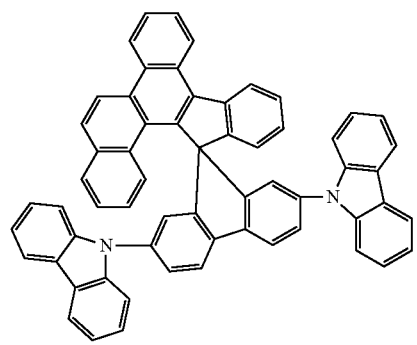
[C-4]
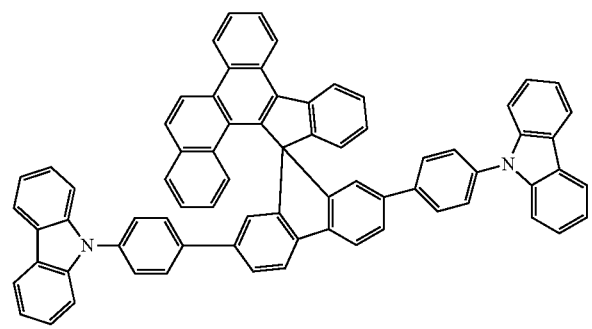

[C-5]
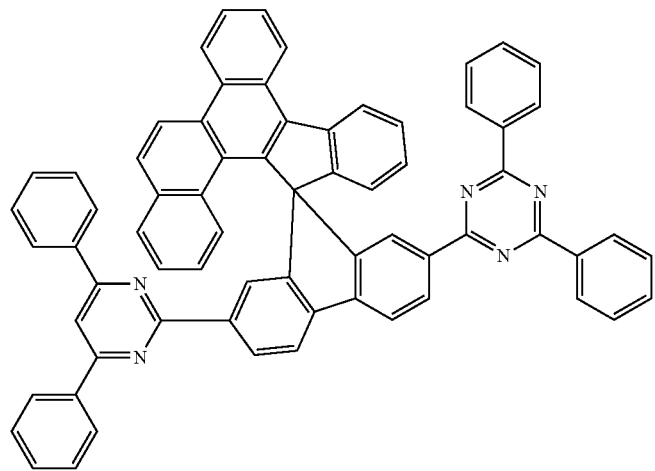
[C-6]
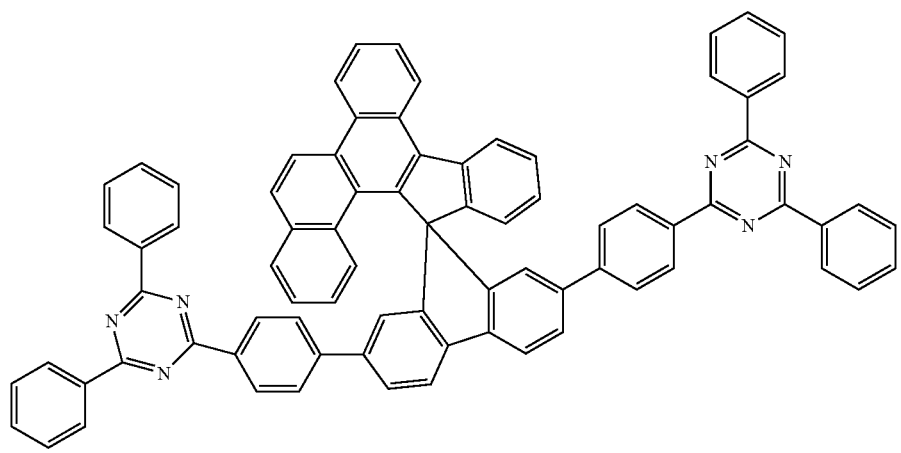
[C-7]
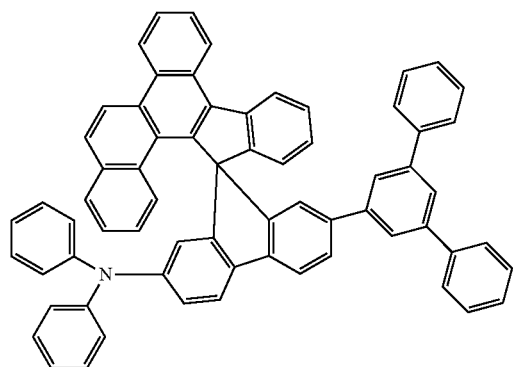
[C-8]
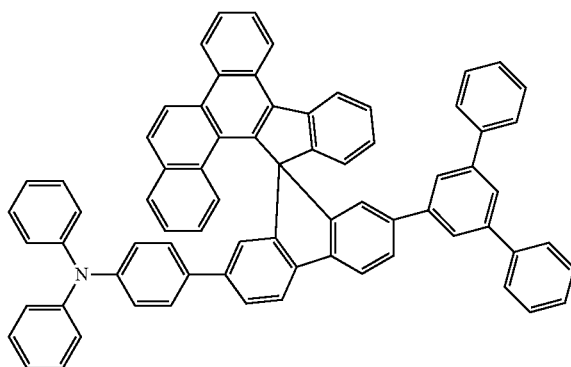

-continued
[C-9] 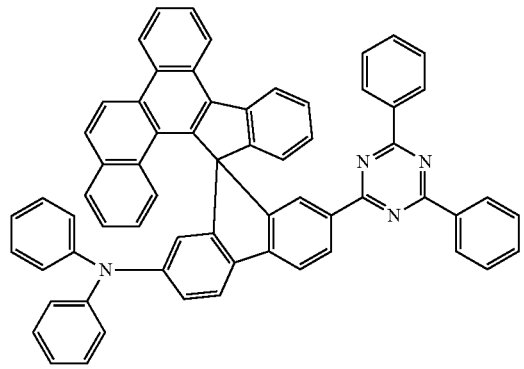
[C-10] 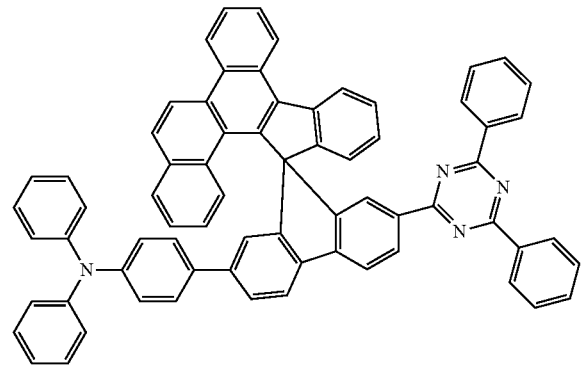
[C-11] 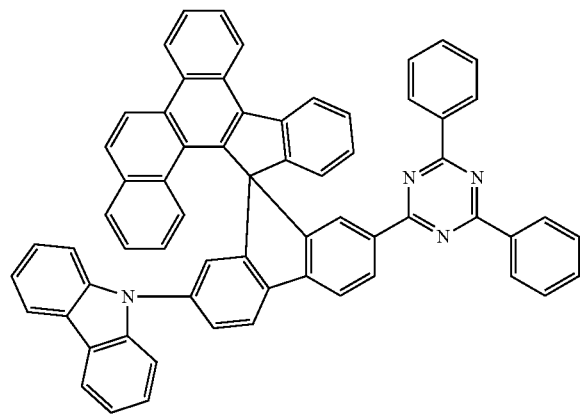
[D-1] 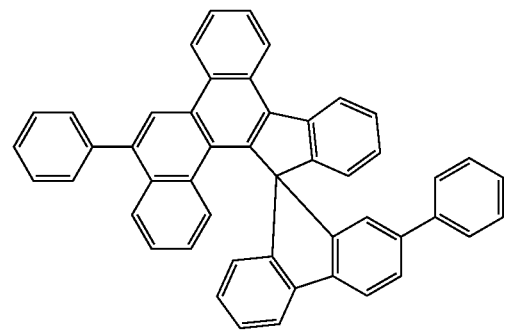
[D-2] 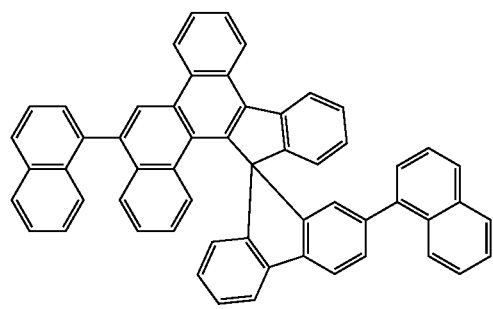
[D-3] 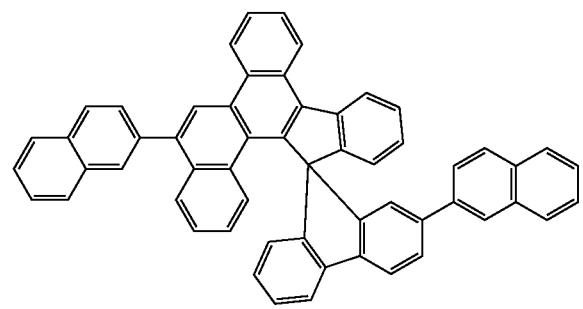
[D-4] 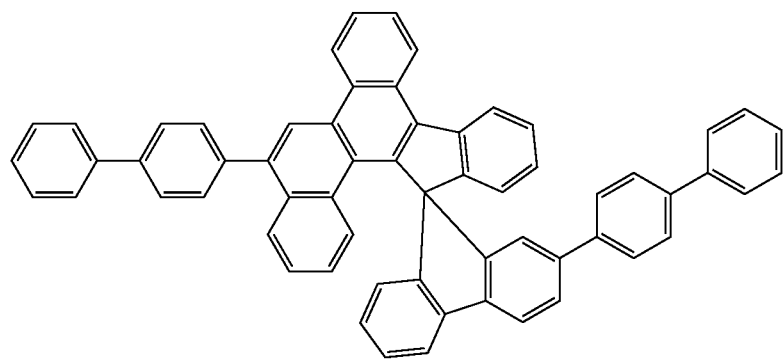

-continued
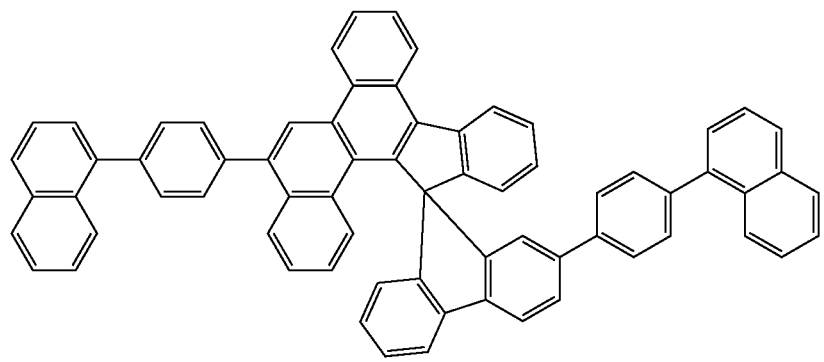
[D-5]
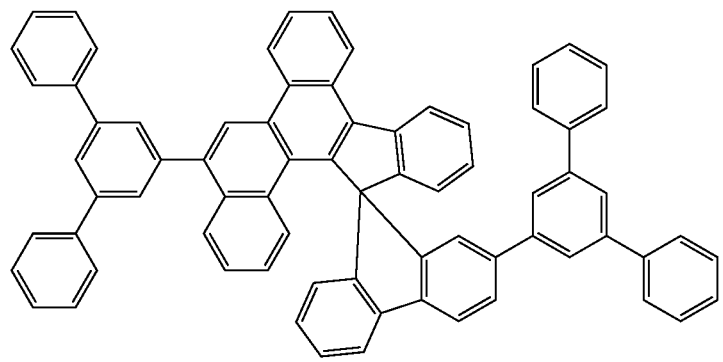
[D-6]
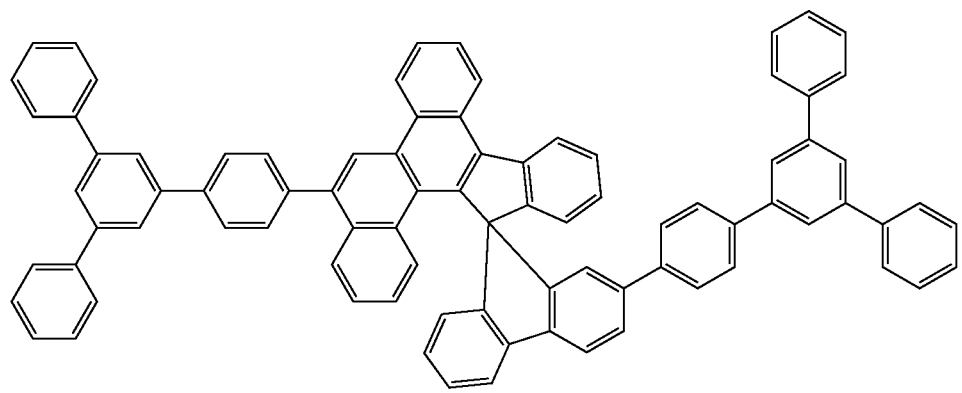
[D-7]
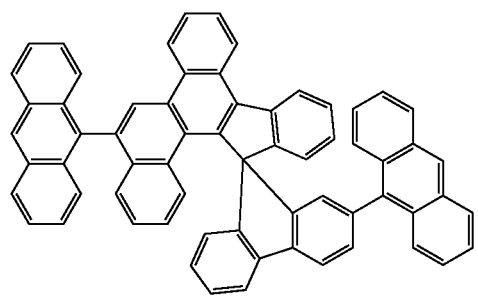
[D-8]
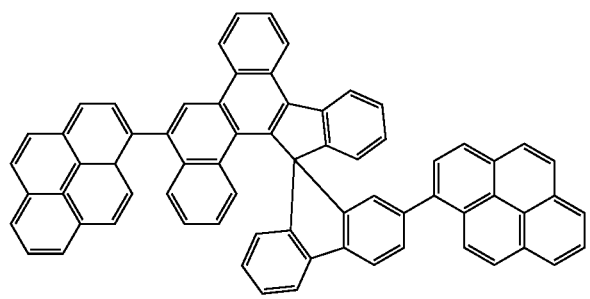
[D-9]

[D-10]
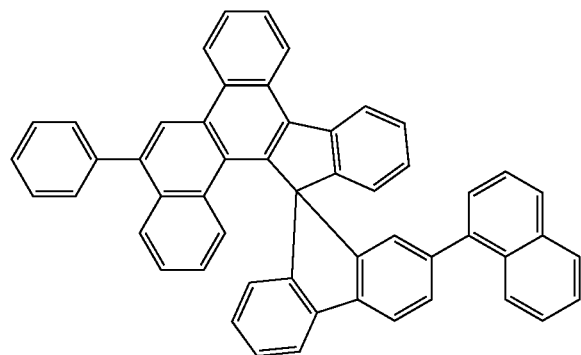
[D-11]
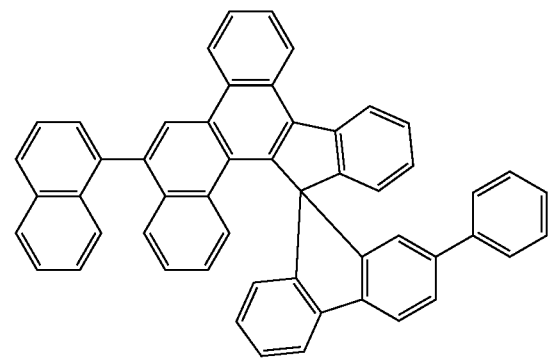
[D-12]
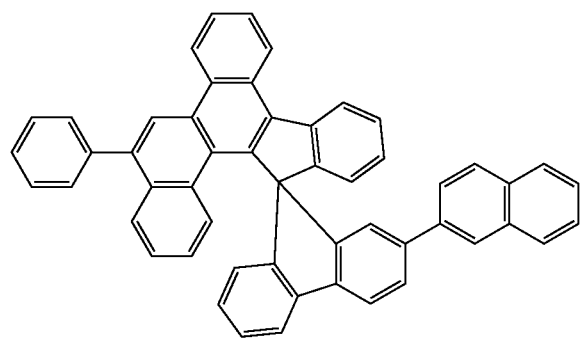
[D-13]
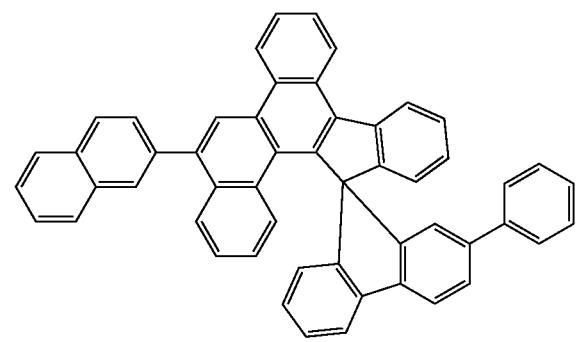
[D-14]
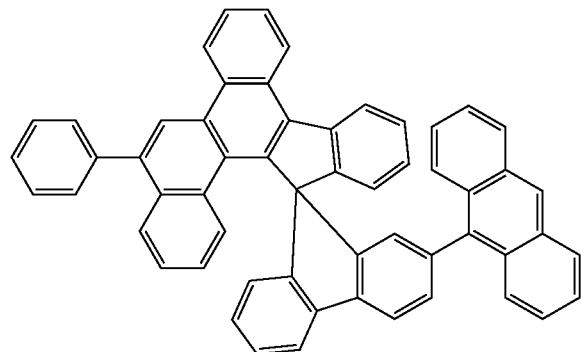
[D-15]
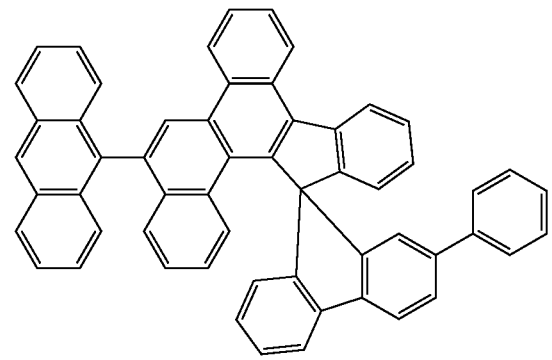
[D-16]
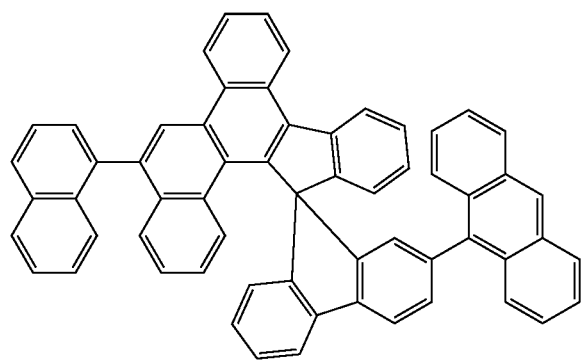
[D-17]
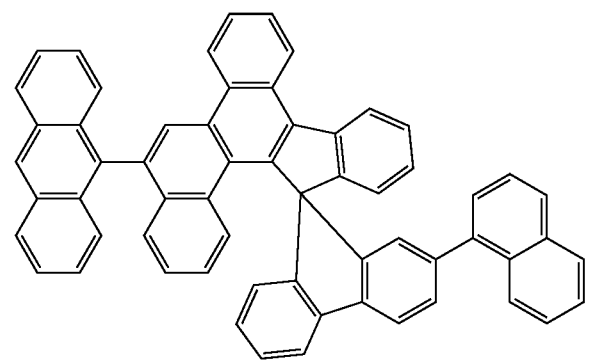

[D-18]
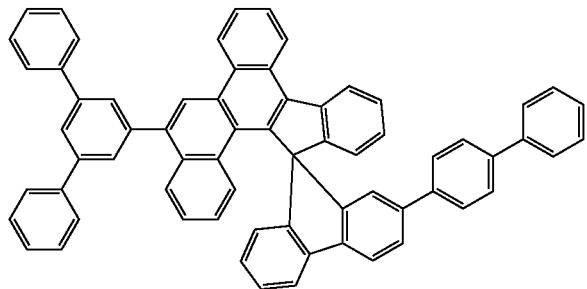
[E-1]
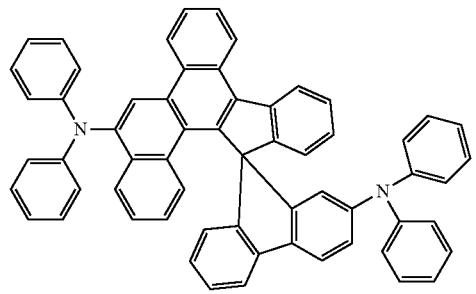
[E-2]
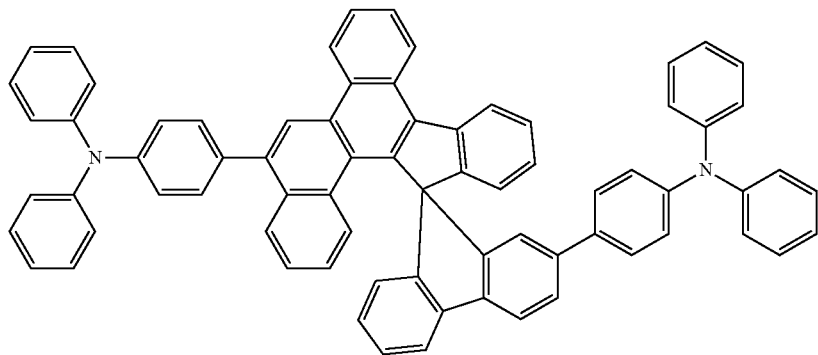
[E-3]
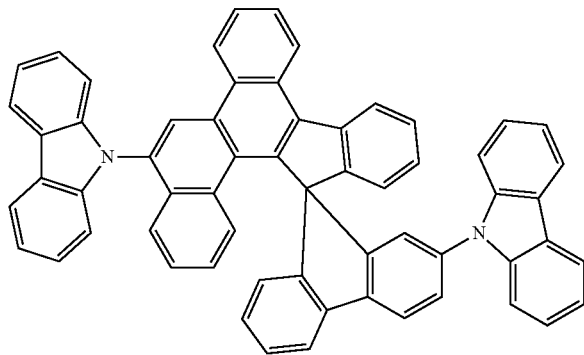
[E-4]
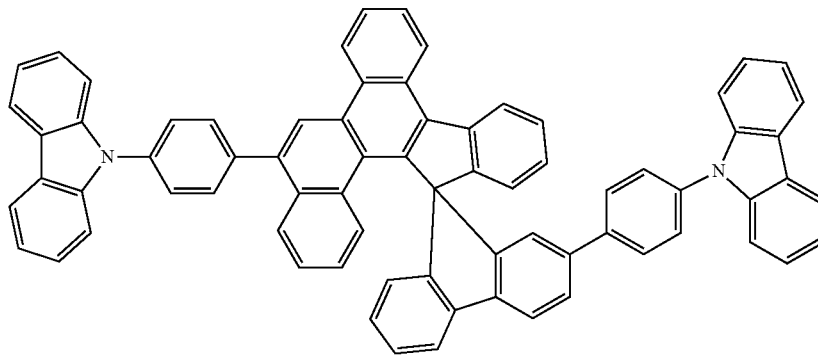

[E-5]
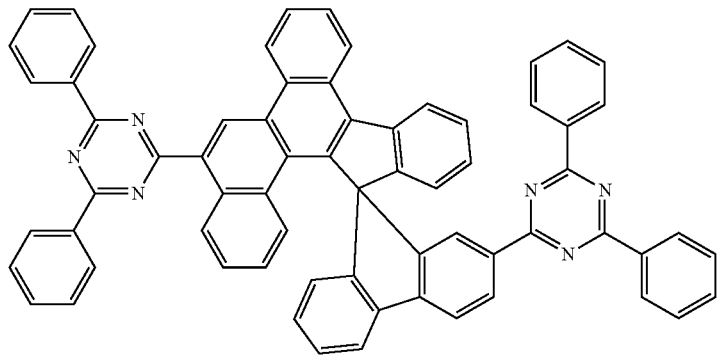
[E-6]
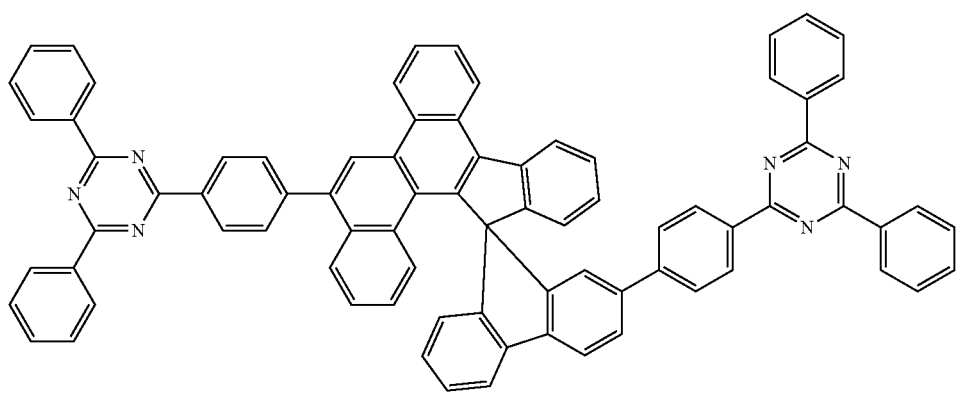
[E-7] [E-8]
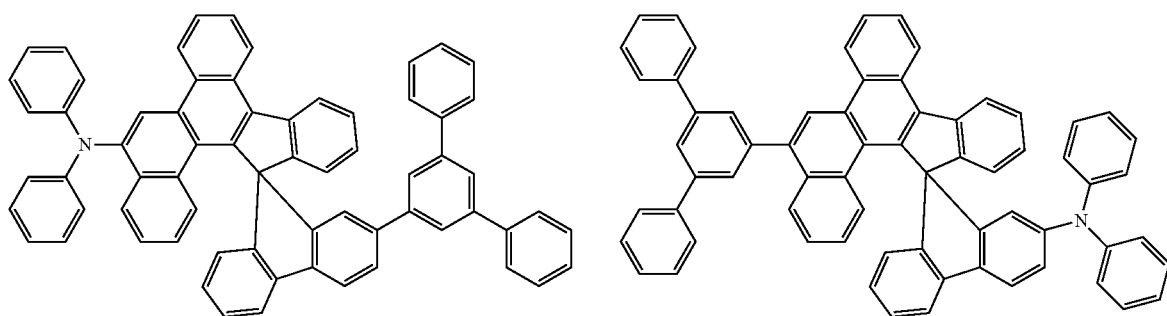
[E-9]
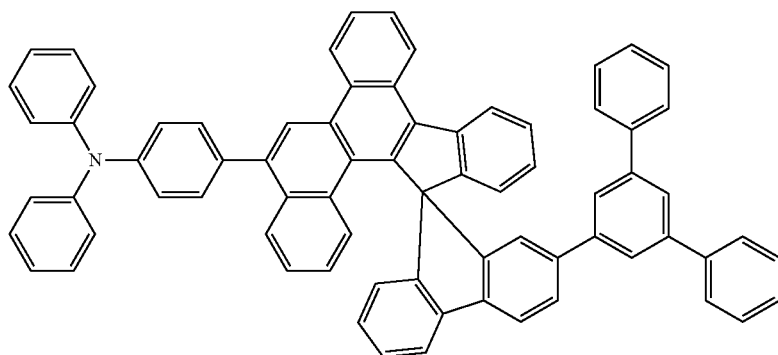

-continued

[E-10] [E-11]

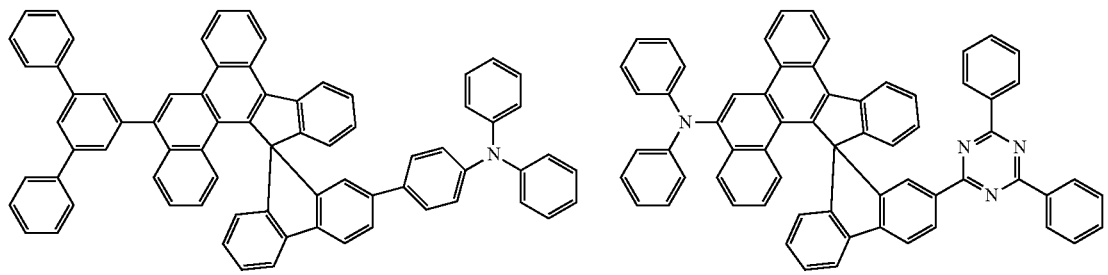

[E-12]

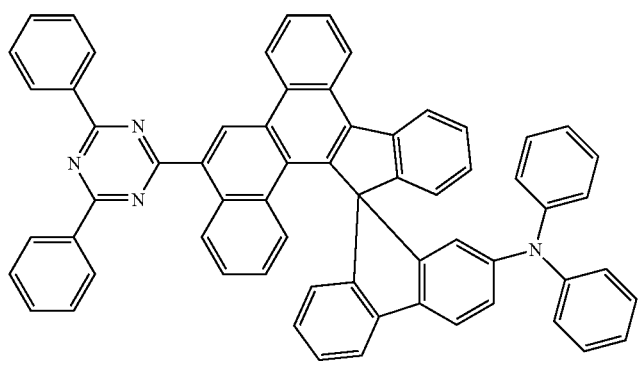

[E-13]

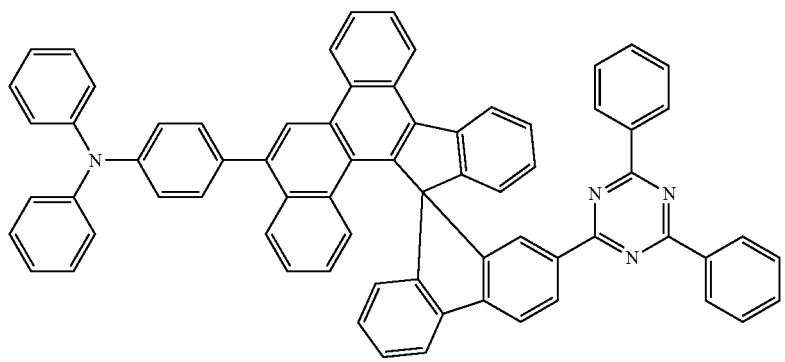

[E-14] [E-15]

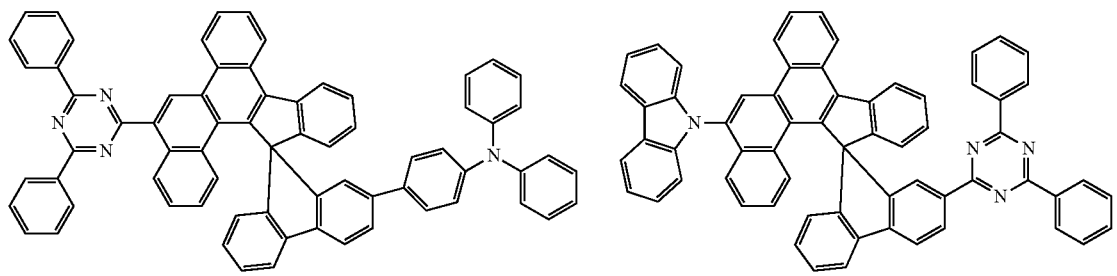

According to another embodiment, an organic optoelectronic device includes an anode and a cathode facing each other and at least one organic layer between the anode and the cathode, wherein the organic layer includes the compound.

The organic layer may include an emission layer and the emission layer may include the compound.

The compound has improved light emitting characteristics in a blue light emitting region and excellent thermal stability, and may improve efficiency when applied to an organic optoelectronic device.

DETAILED DESCRIPTION

Figure 1:
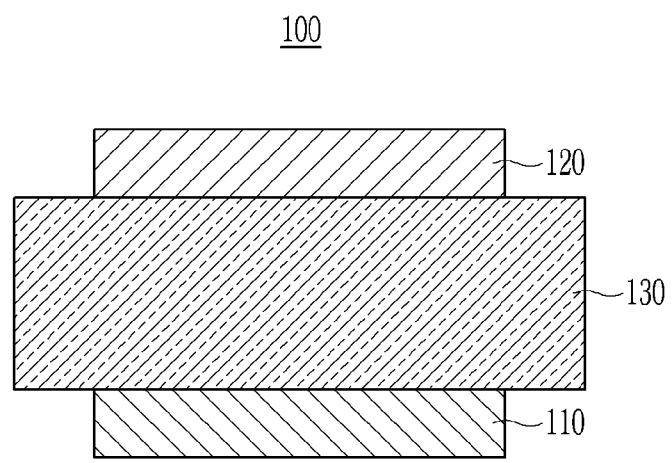
FIG. 1 is a schematic cross-sectional view showing an organic light emitting diode according to an embodiment.

Hereinafter, embodiments of the present invention are described in detail. However, these embodiments are exemplary, the present invention is not limited thereto, and the present invention is defined by the scope of claims.

As used herein, when a definition is not otherwise provided, the term "substituted" refers to replacement of at least one hydrogen of a substituent or a compound by deuterium, an amino group, a substituted or unsubstituted C1 to C30 amine group, a nitro group, a C1 to C40 silyl group, a C1 to C30 alkyl group, a C1 to C10 alkylsilyl group, a C3 to C30 cycloalkyl group, a C3 to C30 heterocycloalkyl group, a C6 to C30 aryl group, a C1 to C20 alkoxy group, a fluoro group, or a C1 to C10 trifluoroalkyl group such as a trifluoromethyl group or a cyano group.

As used herein, when a definition is not otherwise provided, "hetero" refers to one including one to three heteroatoms selected from N, O, S, P, and Si, and remaining carbons in one functional group.

According to one embodiment, a compound for an organic optoelectronic device is represented by Chemical Formula 1.

[Chemical Formula 1]

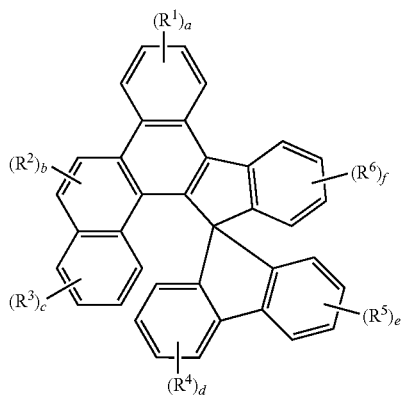

In Chemical Formula 1, $R^1$ to $R^5$ are independently hydrogen, deuterium, —$NH_2$, a substituted or unsubstituted C1 to C30 alkylamine group, a substituted or unsubstituted C6 to C30 arylamine group, a substituted or unsubstituted C1 to C30 alkyl group, a substituted or unsubstituted C6 to C30 aryl group, a substituted or unsubstituted C2 to C30 heteroaryl group, or a combination thereof, at least one of $R^2$, $R^4$, and $R^5$ is a substituted or unsubstituted C6 to C30 aryl group, a substituted or unsubstituted C6 to C30 arylamine group, or a substituted or unsubstituted C2 to C30 heteroaryl group, each of a, c, d, e, and f are an integer of 1 to 4, and b is an integer of 1 or 2.

The compound may include spiro[9H-fluorene-9,15'-[15H]indeno[2,1-g]chrysene] formed by fusing chrysene and spirofluorene as a core structure. In the core structure, the chrysene and the spirofluorene are three-dimensionally overlapped with each other. When the spirofluorene is present in this way, a fluorene moiety may be twisted at an angle of about 90° and thus prevents packing of molecules and suppresses formation of an excimer during formation of a thin film.

In Chemical Formula 1, at least one $R^4$ and at least one $R^5$ may be selected from a substituted or unsubstituted C6 to C30 aryl group, a substituted or unsubstituted C6 to C30 arylamine group, a substituted or unsubstituted C2 to C30 heteroaryl group, and a combination thereof. At least one o $R^4$ and at least one $R^5$ may be present at position Nos. 2 and 7 (meta positions) of the fluorine forming the spiro structure.

In Chemical Formula 1, at least one $R^2$ and at least one $R^5$ may be selected from a substituted or unsubstituted C6 to C30 aryl group, a substituted or unsubstituted C6 to C30 arylamine group, a substituted or unsubstituted C2 to C30 heteroaryl group, and a combination thereof. At least $R^2$ may be present at a position No. 12 (a meta position) of the chrysene, and at least one $R^5$ may be present at a position No. 2 or 7 (meta positions) of the fluorine forming the spiro structure.

Examples of the C2 to C30 heteroaryl group may be carbazole, phenothiazine, phenoxazine, acridine, triazine, and the like.

In Chemical Formula 1, the combination indicates that the substituents are connected with each other and thus form a fused ring or are linked by a single bond or through methylene.

Specific examples of the compound represented by Chemical Formula 1 may be compounds of Chemical Formulae A-1 to E-15.

[A-1]
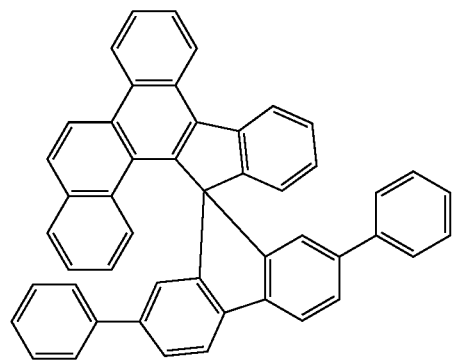
[A-2]
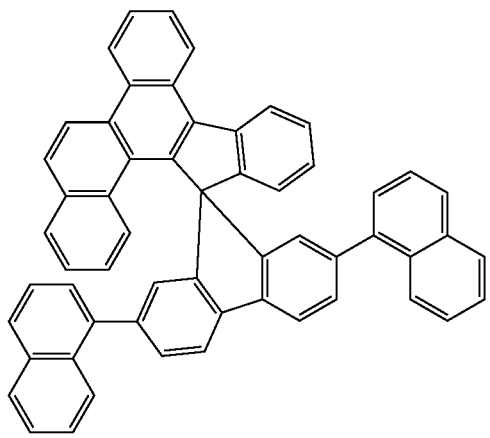
[A-3]
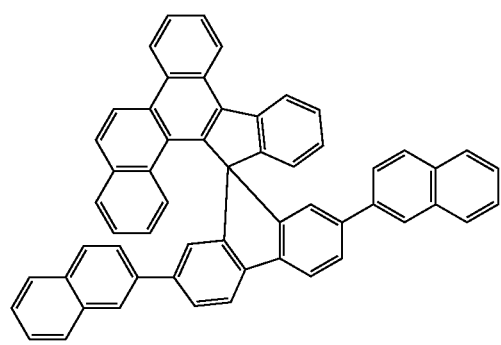
[A-4]
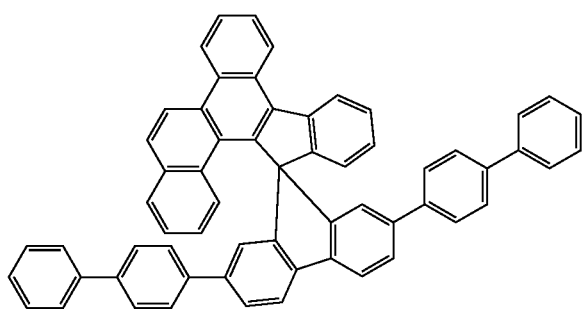
[A-5]
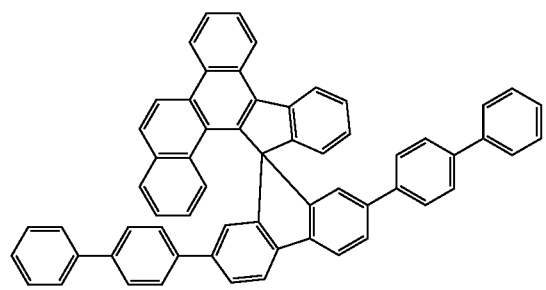
[A-6]
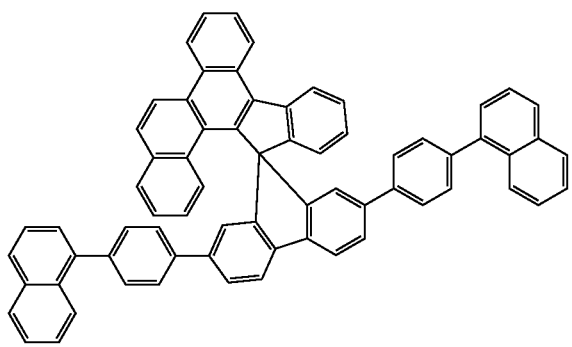
[A-7]
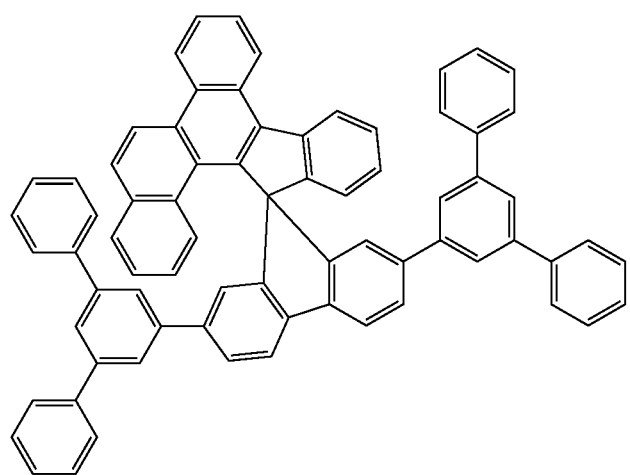

-continued
[A-8]
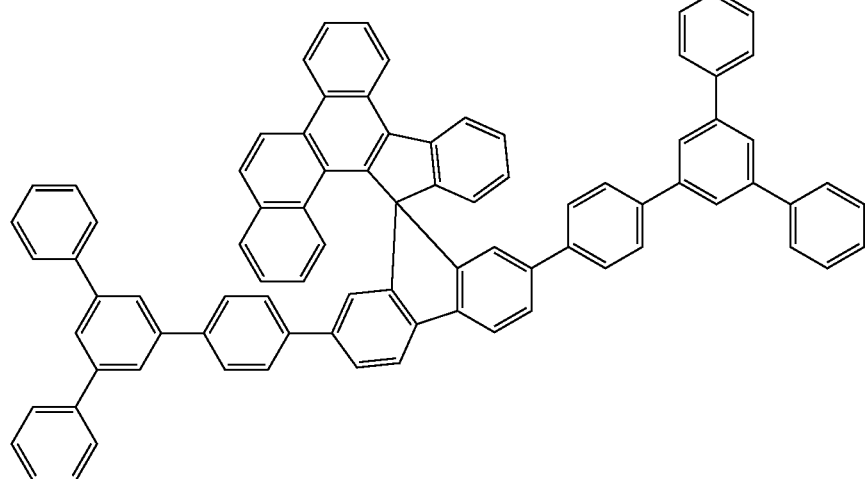
[A-9]
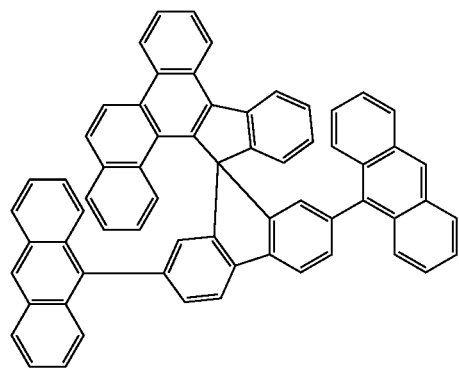
[A-10]
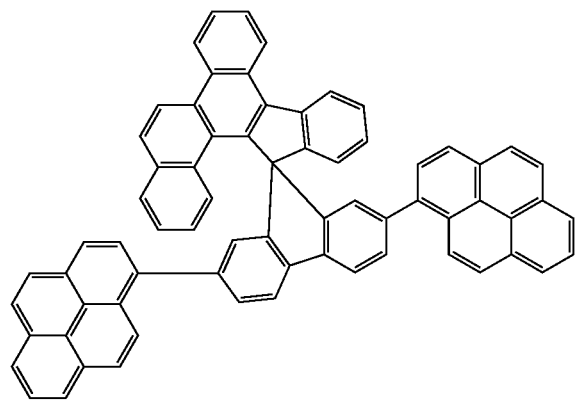
[B-1]
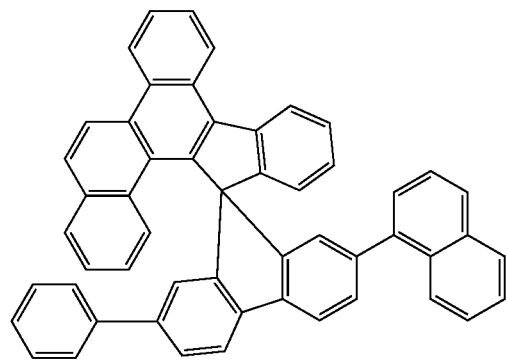
[B-2]
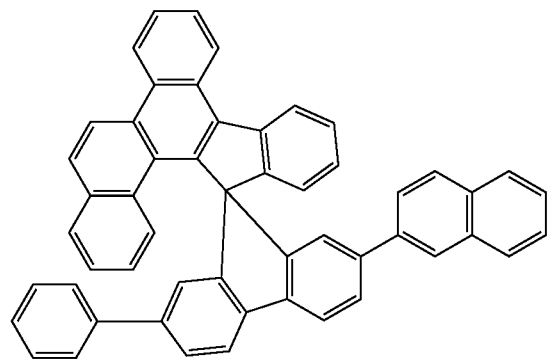

-continued
[B-3]
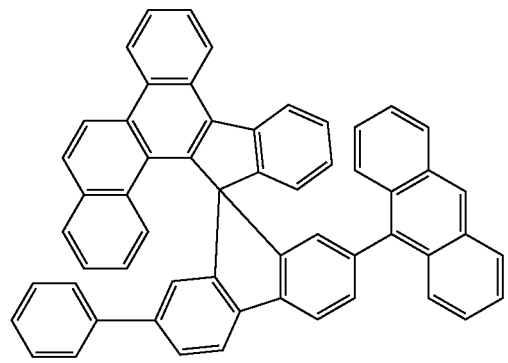
[B-4]
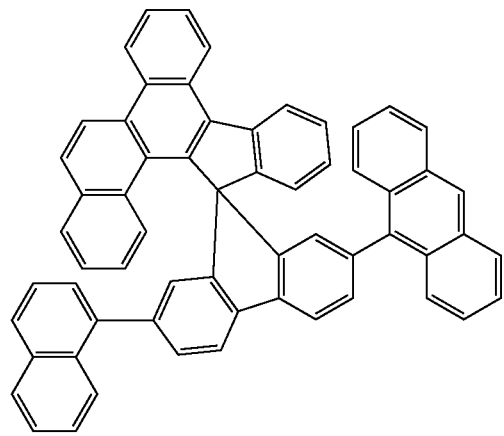
[B-5]
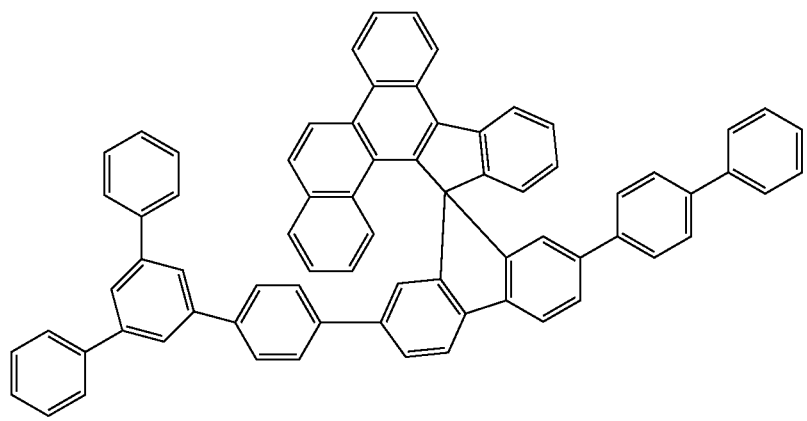
[C-1]
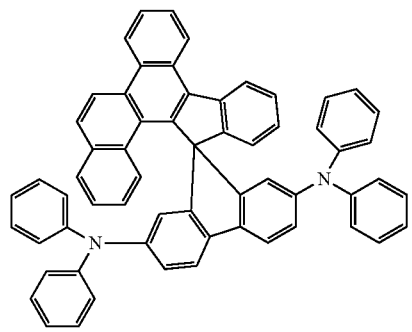
[C-2]
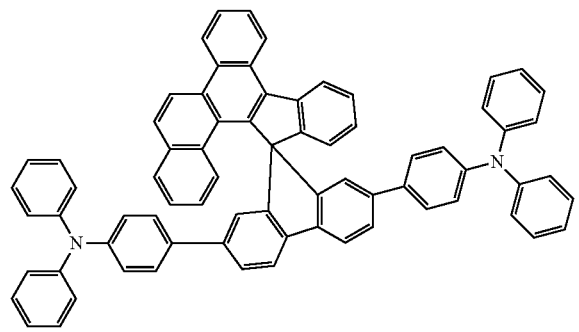
[C-3]
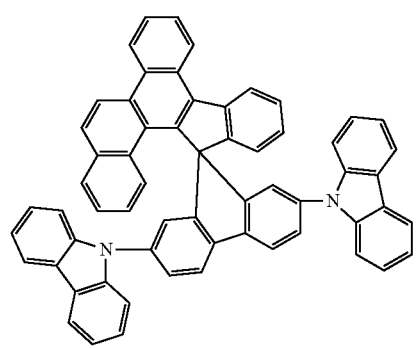
[C-4]
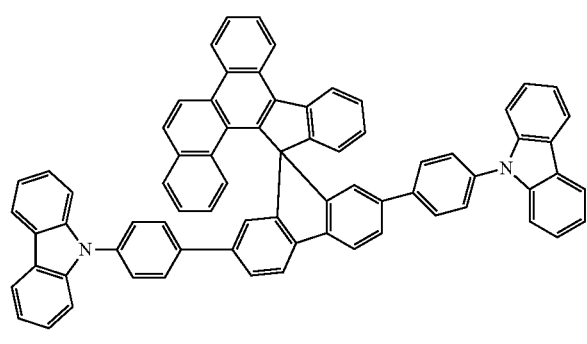

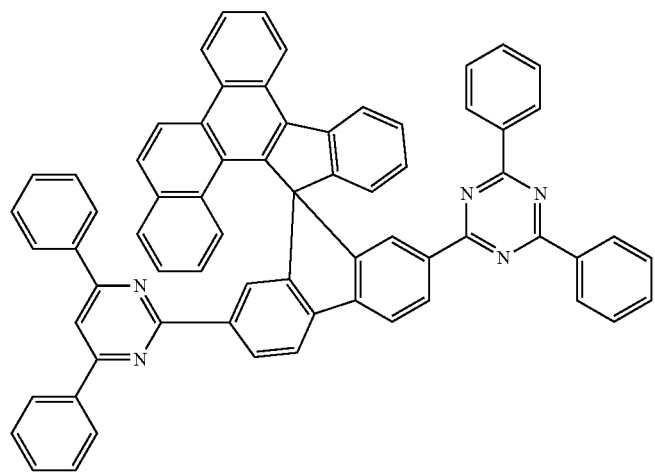
[C-5]
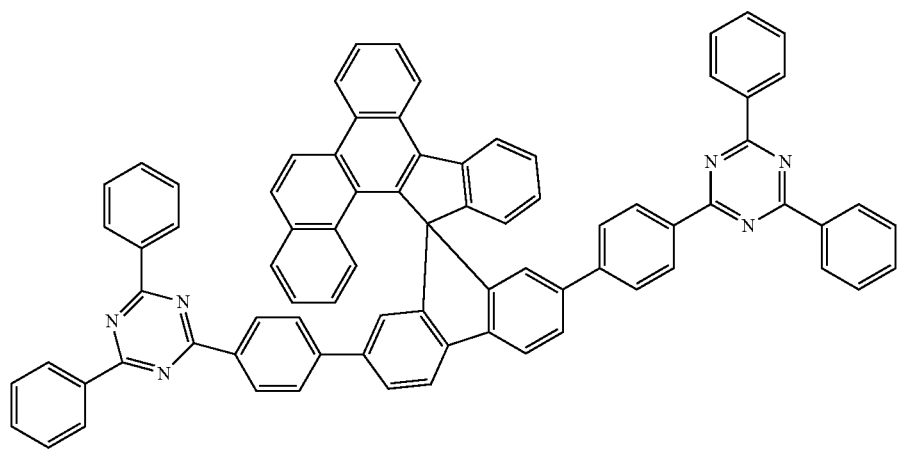
[C-6]
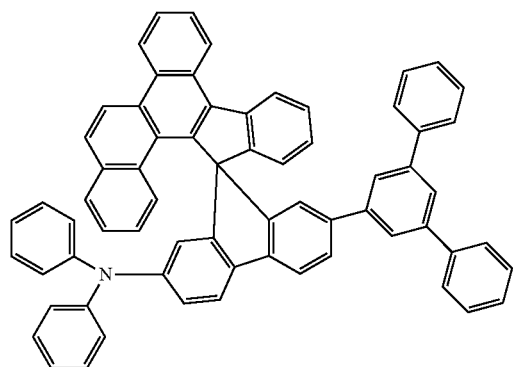
[C-7]
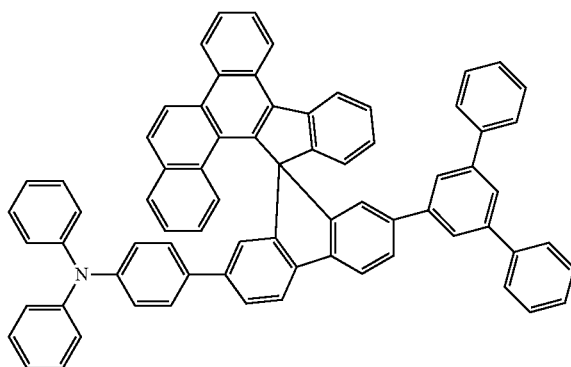
[C-8]

[C-9]
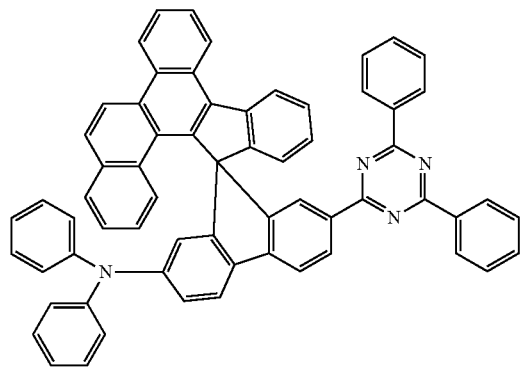
[C-10]
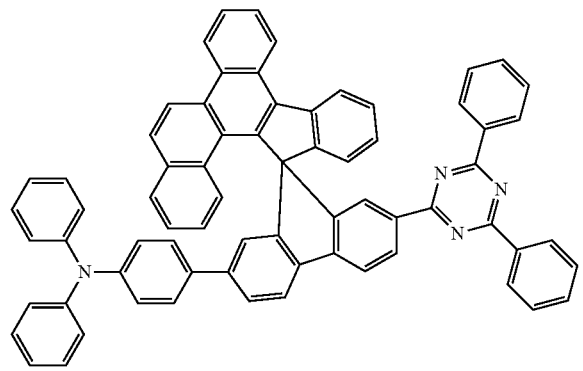
[C-11]
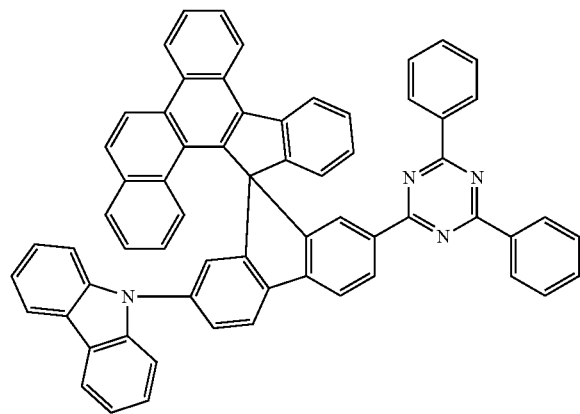
[D-1]
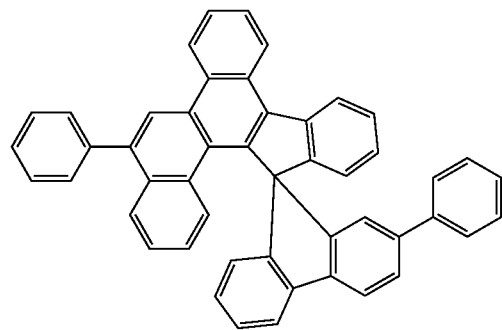
[D-2]
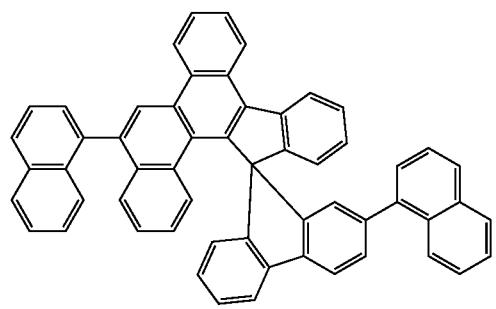
[D-3]
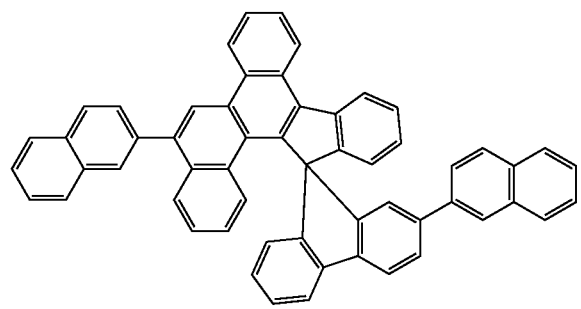
[D-4]
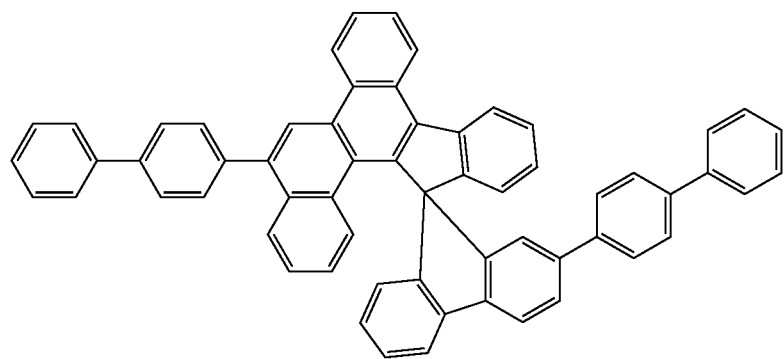

-continued
[D-5]
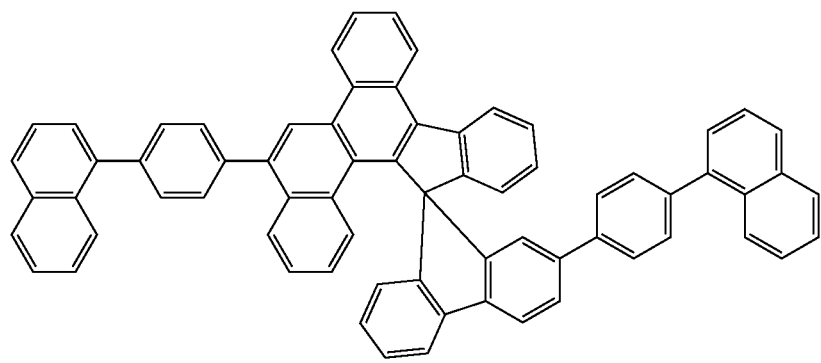
[D-6]
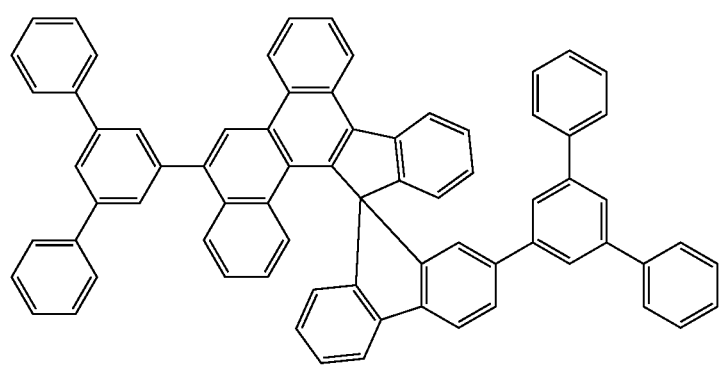
[D-7]
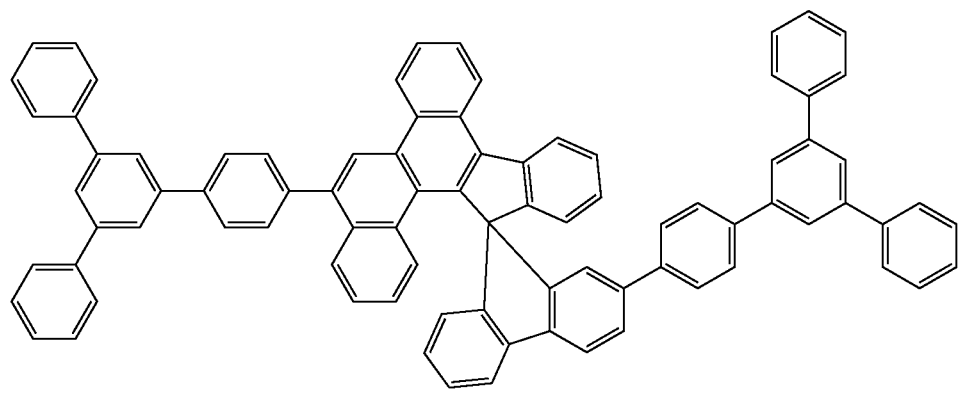
[D-8]
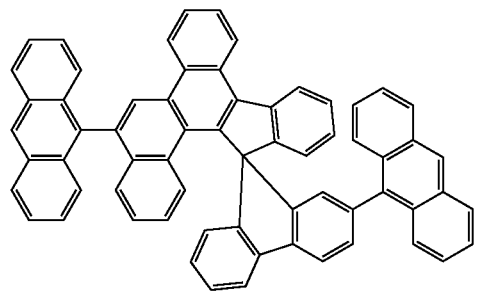
[D-9]
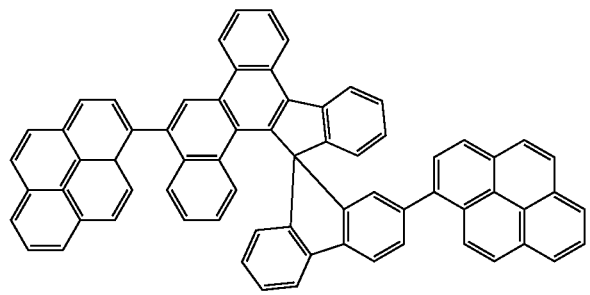

-continued
[D-10]
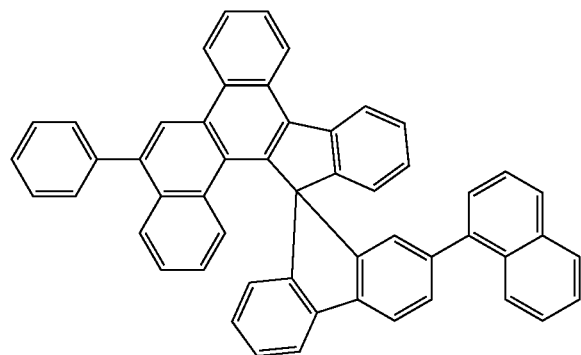
[D-11]
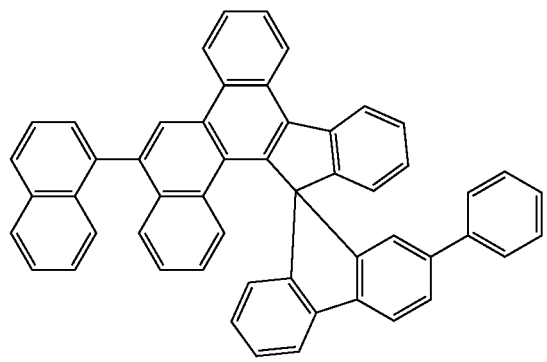
[D-12]
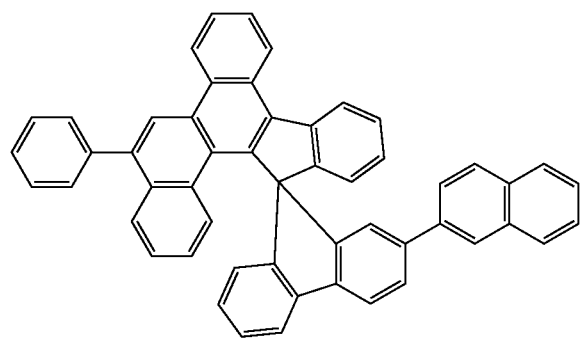
[D-13]
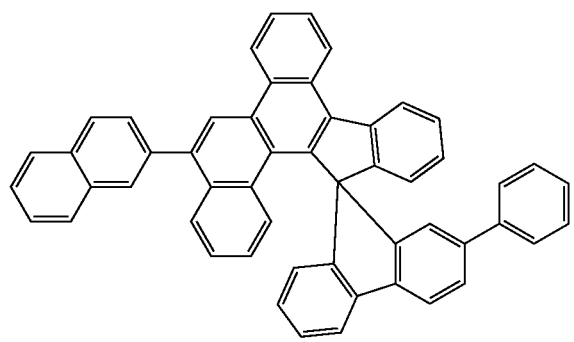
[D-14]
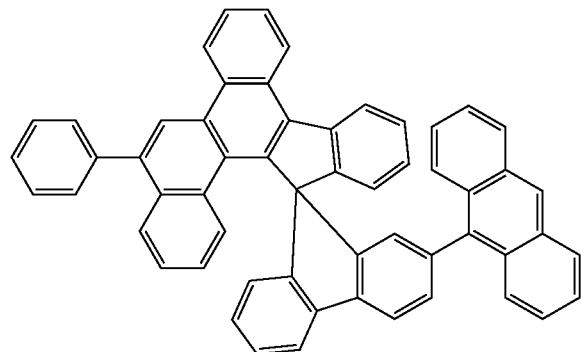
[D-15]
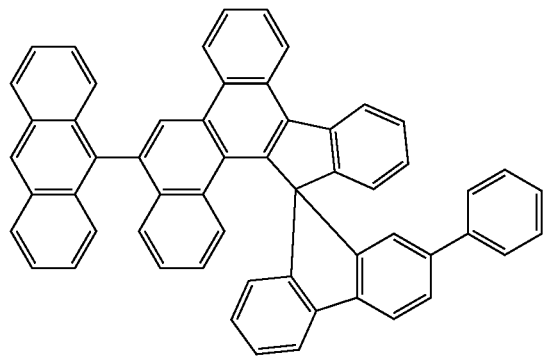
[D-16]
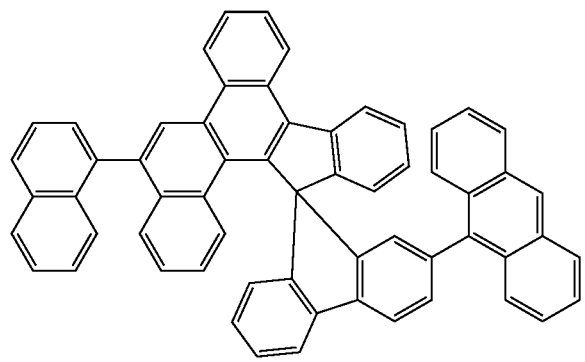
[D-17]
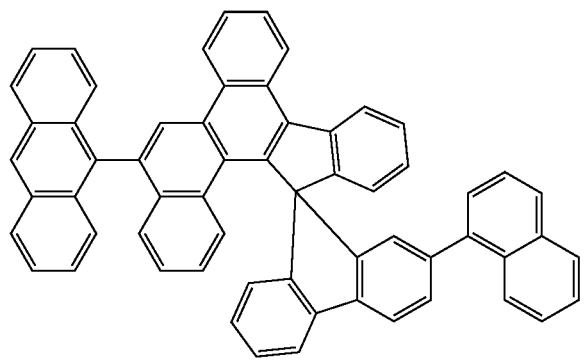

-continued
[D-18]
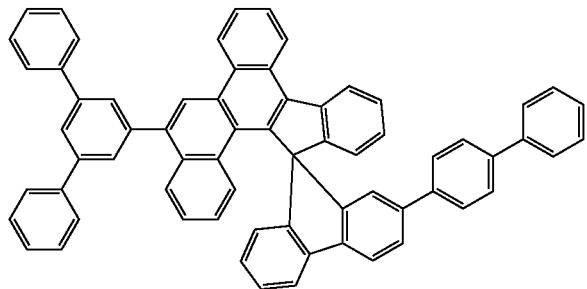
[E-1]
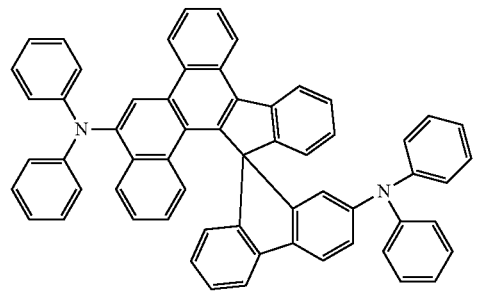
[E-2]
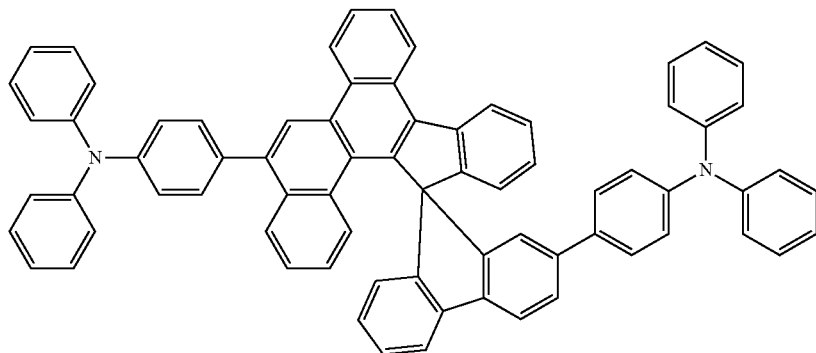
[E-3]
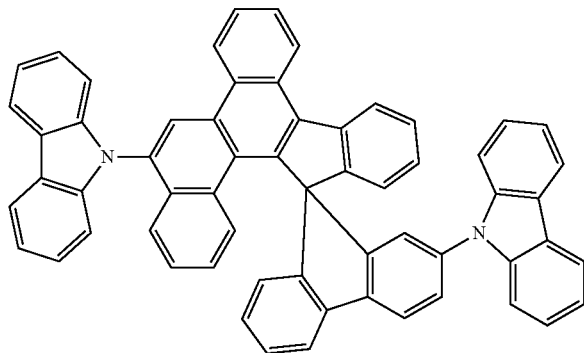
[E-4]
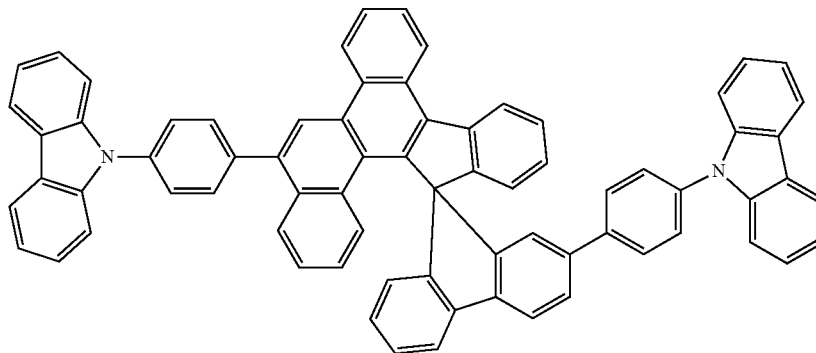

[E-5]
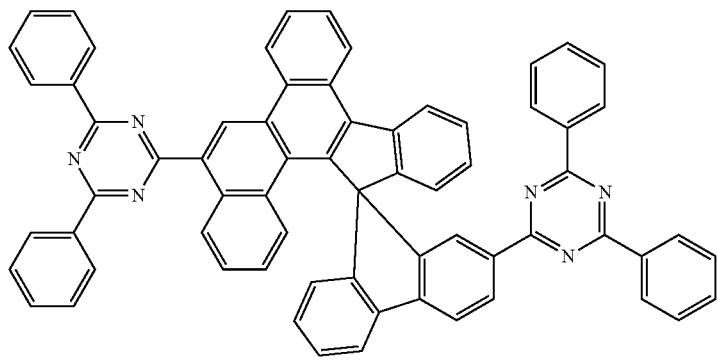
[E-6]
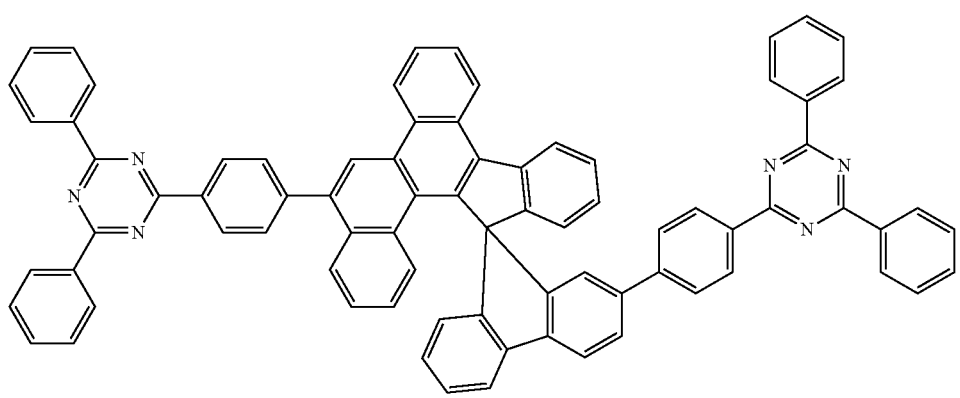
[E-7] [E-8]
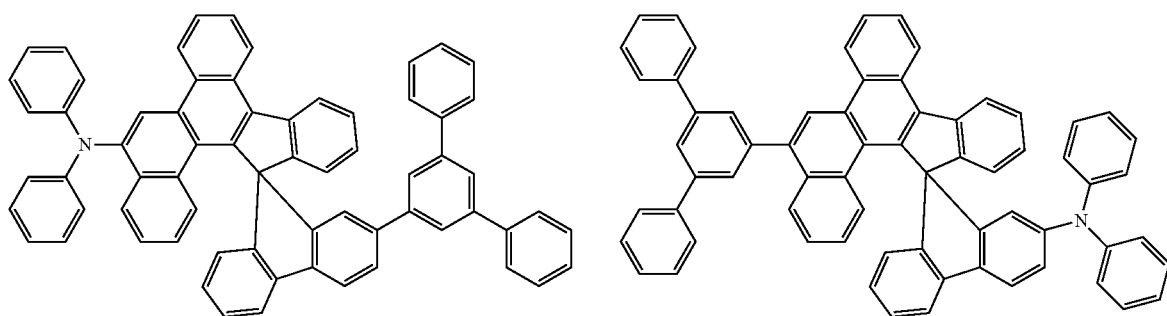
[E-9]
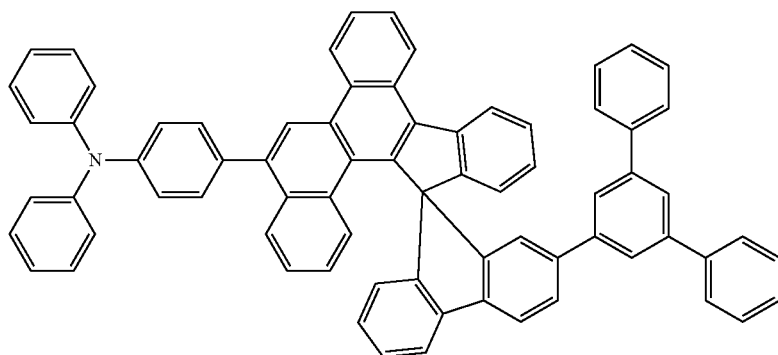

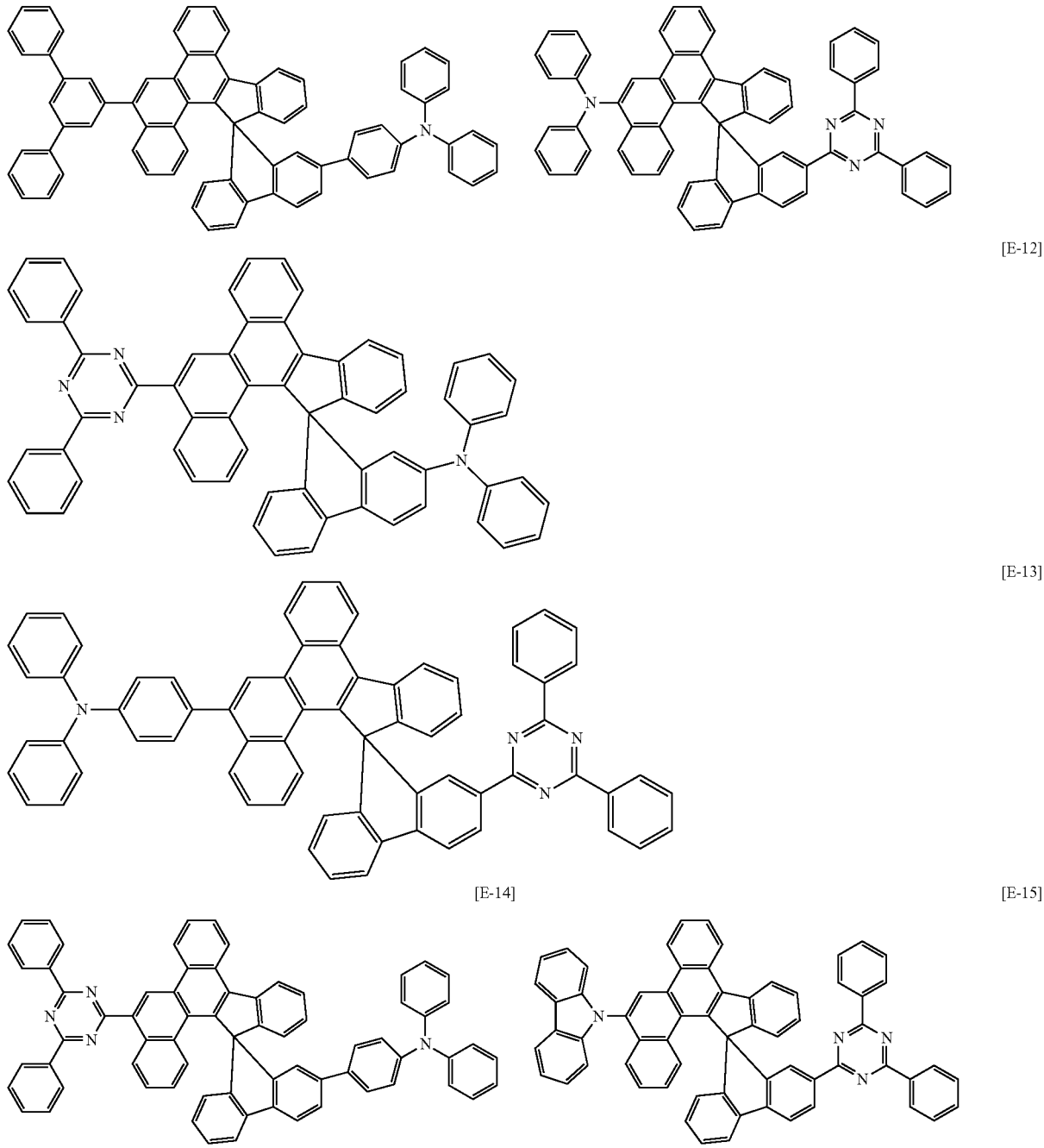

The compound may have a maximum absorption wavelength of about 380 nm to about 460 nm, for example about 395 nm to about 454 nm.

The compound may have a bandgap of about 2.2 eV to about 3.0 eV, for example about 2.3 eV to about 2.9 eV.

When at least one of $R^1$ to $R^5$ is selected from a substituted or unsubstituted C1 to C30 alkylamine group, a substituted or unsubstituted C6 to C30 arylamine group, a substituted or unsubstituted C2 to C30 N-containing a heteroaryl group, and a combination thereof, the compound includes an electron donor functional group and an electron acceptor functional group in one molecule and may balance moving of holes and electrons and efficiently form excitons. This compound having bipolar characteristics may well trap the holes and the electrons and facilitate generation of the excitons in an emission layer and thus improve efficiency of an organic optoelectronic device.

In Chemical Formula 1, because at least one of $R^2$, $R^4$, and $R^5$ is a aromatic substituent of a substituted or unsubstituted C6 to C30 aryl group, a substituted or unsubstituted C6 to C30 arylamine group, or a substituted or unsubstituted C2 to C30 heteroaryl group, thermal stability is more improved compared with when $R^2$, $R^4$, and $R^5$ are hydrogen or an aliphatic substituent. Accordingly, the compound may secure excellent film-forming workability and stably maintain efficiency of a photoelectronic device in a subsequent process.

In addition, the compound may not have a planar structure but a three-dimensional core structure and thus prevents packing of molecules and resultantly improves efficiency of an organic optoelectronic device.

The compound may be applied to various organic optoelectronic devices, for example, may be used as a host. This compound may be obtained in a dry process such as a chemical vapor deposition (CVD) method or in a solution process.

Hereinafter, an organic optoelectronic device manufactured by using the compound is described.

The organic optoelectronic device may be any device that converts electrical energy into photoenergy and vice versa without particular limitation, and may be, for example, an organic photoelectric device, an organic light emitting diode, and an organic solar cell.

The organic optoelectronic device includes an anode and a cathode facing each other, and at least one organic layer between the anode and the cathode, wherein the organic layer includes the compound.

Herein, an organic light emitting diode as one example of an organic optoelectronic device is described referring to drawings.

FIG. 1 is a cross-sectional view showing an organic light emitting diode according to an embodiment.

Referring to FIG. 1, an organic light emitting diode 100 according to an embodiment includes a first electrode 110 and a second electrode 120 facing each other, and an organic layer 130 between the first electrode 110 and the second electrode 120.

One of the first electrode 110 and the second electrode 120 is a cathode and the other is an anode.

At least one of the first electrode 110 and the second electrode 120 may be a transparent electrode. For example, when the first electrode 110 is a transparent electrode, the organic light emitting diode 100 may be a bottom emission type in which light is emitted toward the first electrode 110, while when the second electrode 120 is a transparent electrode, the organic light emitting diode 100 may be a top emission type in which light is emitted toward the second electrode 120. In addition, when the first electrode 110 and the second electrode 120 are both transparent electrodes, both-side emission is realized.

The organic layer 130 may include the compound. The organic layer 130 may include at least one layer, and may include an emission layer.

The emission layer may include the compound, for example the compound alone, a mixture of at least two kinds of the compound, or a mixture of the compound and another compound.

The organic layer 130 may further include an auxiliary layer in addition to the emission layer. The auxiliary layer may improve luminous efficiency, and may be disposed at at least one of between the first electrode 110 and the emission layer and between the second electrode 120 and the emission layer. The auxiliary layer may include at least one layer of an electron transport layer and a hole transport layer for balancing between electrons and holes, and an electron injection layer and a hole injection layer for reinforcing injection of electrons and holes.

The organic light emitting diode may be applied to an organic light emitting display device.

Hereinafter, the embodiments are illustrated in more detail with reference to examples. These examples, however, are not in any sense to be interpreted as limiting the scope of the invention.

Comparative Synthesis Example 1: Synthesis of Compound Represented by Chemical Formula 2

[Chemical Formula 2]

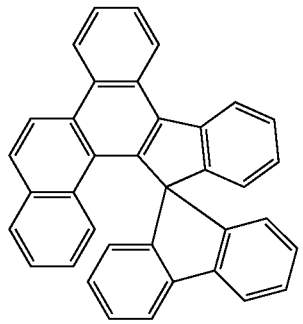

[Reaction Scheme 1]

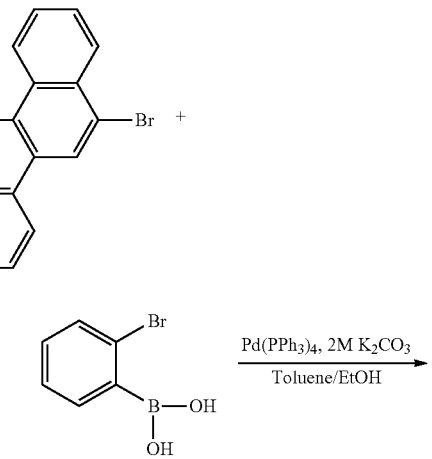

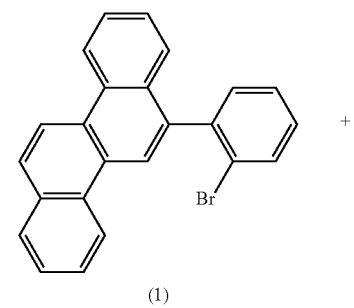

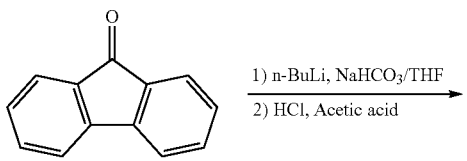

-continued

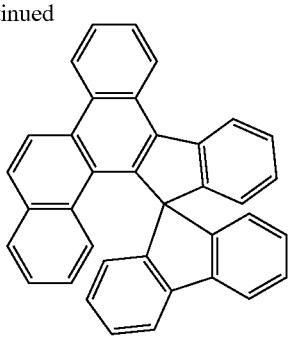

(1) Synthesis of Compound 1

6-bromochrysene (4.00 g, 13.0 mmol), 2-bromophenyl boronic acid (3.14 g, 10.4 mmol), and Pd(PPh$_3$)$_4$ (0.60 g, 0.52 mmol) were dissolved in 350 mL of anhydrous toluene and 50 mL of an anhydrous ethanol solvent under a nitrogen atmosphere to prepare a mixture. 50 mL of a 2M K$_2$CO$_3$ solution was added to the mixture. The obtained mixture was heated for 40 minutes while being refluxed under the nitrogen atmosphere. When a reaction was complete, the resultant was extracted with chloroform and distilled water, and then treated with anhydrous magnesium sulfate. The obtained resulting material was purified through a silica gel column by using toluene:hexane (a volume ratio of 1:10) as an eluting solvent to obtain 0.75 g of a white solid (a yield of 15.0%).

(2) Synthesis of Compound Represented by Chemical Formula 2

Compound 1 (1.00 g, 2.61 mmol) was dissolved in 50 mL of an anhydrous tetrahydrofuran solvent under a nitrogen atmosphere. 1.87 mL of a 2M normal butyl lithium solution was slowly added thereto at −78° C. 9-fluorenone (0.56 g, 3.10 mmol) dissolved in 20 mL of an anhydrous tetrahydrofuran solvent was added thereto. When a reaction was complete, 30 mL of a 2N sodium bicarbonate aqueous solution was added thereto at room temperature. The obtained mixture was extracted with chloroform and distilled water and treated with anhydrous magnesium sulfate. The solvents were evaporated from the obtained liquid by using an evaporator, and a yellow solid obtained therefrom was dissolved in 100 mL of acetic acid. 10 mL of a HCl aqueous solution was added thereto, and the obtained mixture was heated while being refluxed for 1 hour. When a reaction was complete, the resultant was extracted with chloroform and distilled water and treated with anhydrous magnesium sulfate. The obtained resulting material was purified through a silica gel column by using chloroform:hexane (a volume ratio of 1:3) as an eluting solvent to obtain 0.24 g of a white solid (a yield of 19.7%). [HRMS (FAB+, m/z): cald. For C37H22 466.1721; found, 466.1723].

Synthesis Example 1: Synthesis of Compound Represented by Chemical Formula A-7

[Chemical Formula A-7]

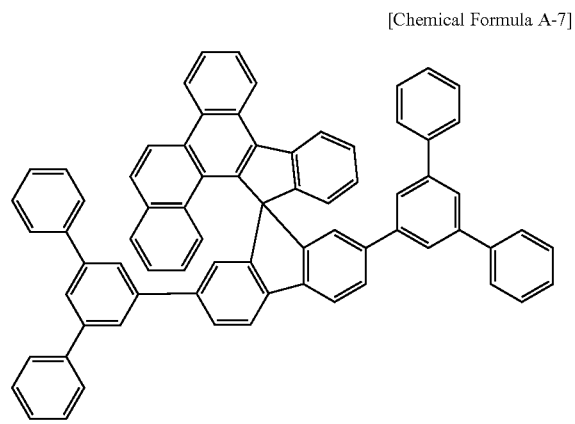 [SMILES: c1ccc(-c2cc(-c3ccccc3)cc(-c3ccc4c(c3)C3(c5cc(-c6cc(-c7ccccc7)cc(-c7ccccc7)c6)ccc5-4)c4ccccc4-c4c3c3c5ccccc5ccc3c3ccccc43)c2)cc1]

[Reaction Scheme 2]

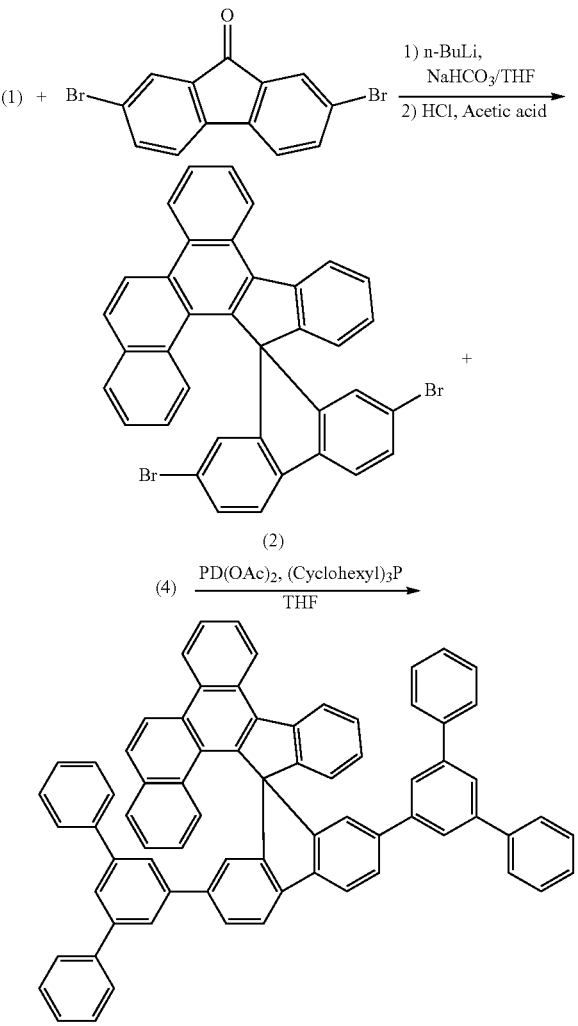

-continued

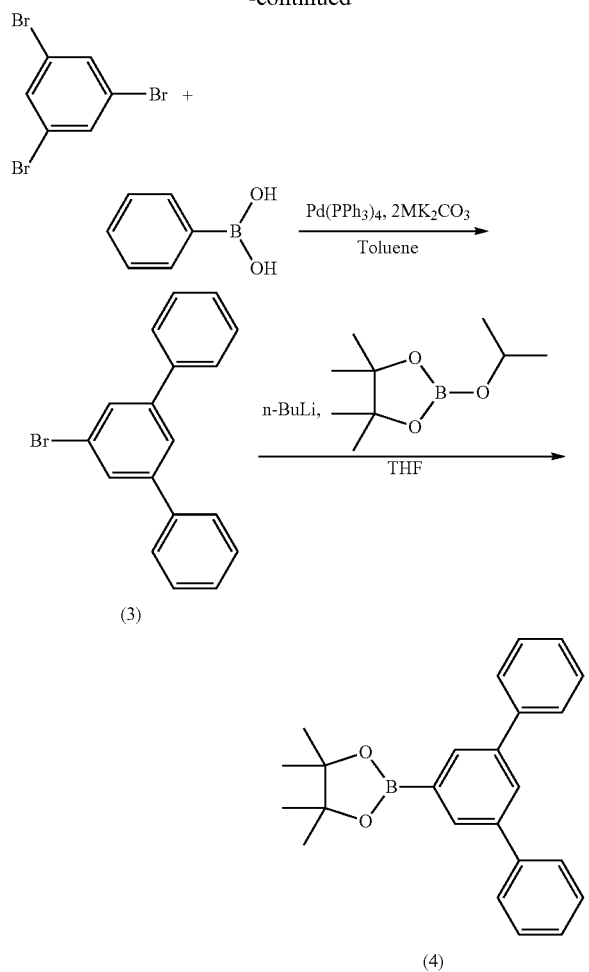

(1) Synthesis of Compound 2

Compound 1 (1.00 g, 2.61 mmol) according to Comparative Synthesis Example 1 was dissolved in 50 mL of an anhydrous tetrahydrofuran solvent under a nitrogen atmosphere. 1.87 mL of a 2M normal butyl lithium solution was slowly added thereto at −78° C. 2,7-dibromo-9-fluorenone (1.04 g, 3.07 mmol) dissolved in 20 mL of an anhydrous tetrahydrofuran solvent was added thereto. When a reaction was complete, 30 mL of a 2N sodium bicarbonate aqueous solution was added thereto at room temperature. The obtained mixture was extracted with chloroform and distilled water and treated with anhydrous magnesium sulfate. The solvents were evaporated from the obtained liquid by using an evaporator to obtain a yellow solid, and the obtained yellow solid was dissolved in 100 mL of acetic acid. 10 mL of a HCl aqueous solution was added thereto, and the obtained mixture was heated for one hour while being refluxed. When a reaction was complete, the resultant was extracted with chloroform and distilled water and treated with anhydrous magnesium sulfate. The obtained resulting material was purified by using chloroform:hexane (a volume ratio of 1:3) as an eluting solvent through a silica gel column to obtain 0.34 g of a white solid (a yield of 21.3%).

(2) Synthesis of Compound Represented by Chemical Formula A-7

Compound 2 (0.30 g, 0.48 mmol), Compound 3 (0.41 g, 1.15 mmol), Pd(OAc)$_2$ (0.008 g, 0.04 mmol), and tricyclohexylphosphine (0.02 g, 0.08 mmol) were dissolved in 100 mL of an anhydrous tetrahydrofuran solvent under a nitrogen atmosphere to prepare a mixture. 10 mL of a 20 wt % tetraethyl ammonium hydroxide aqueous solution was added thereto. The obtained mixture was heated for 3 hours under the nitrogen atmosphere. When a reaction was complete, the resultant was extracted with chloroform and distilled water and treated with anhydrous magnesium sulfate. The obtained resulting material was purified by using chloroform:hexane (a volume ratio of 1:3) as an eluting solvent through a silica gel column to obtain 0.48 g of a white solid (a yield of 54.2%).

[HRMS (FAB+, m/z): cald. For C73H46 922.3600; found, 922.3685].

(3) Synthesis of Compound (3)

1,3,5-tribromobenzene (20 g, 63 mmol) and Pd(PPh$_3$)$_4$ (4.36 g, 3.7 mmol) were dissolved in 500 mL of an anhydrous toluene solvent under a nitrogen atmosphere to prepare a mixture. Phenylboronic acid (17 g, 140 mmol) and 50 mL of a 2M K$_2$CO$_3$ solution were added thereto. The obtained mixture was heated for 5 hours while being refluxed under the nitrogen atmosphere. When a reaction was complete, the resultant was extracted with chloroform and distilled water and treated with anhydrous magnesium sulfate. The obtained resulting material was purified by using chloroform:hexane (a volume ratio of 1:10) as an eluting solvent through a silica gel column to obtain 11.8 g of a white solid (a yield of 60.0%).

(4) Synthesis of Compound 4

Compound 3 (10.0 g, 32.3 mmol) was dissolved in 400 mL of an anhydrous tetrahydrofuran solvent under a nitrogen atmosphere. 24.3 mL of a 2M normal butyl lithium solution and 9.9 mL of isopropoxy-4,4,5,5-tetramethyl-1,3,2-dioxaborolane were added thereto at −78° C., and the obtained mixture was stirred for 2 hours. When a reaction was complete, the resultant was extracted with chloroform and distilled water and treated with anhydrous magnesium sulfate. The obtained resulting material was reprecipitated by using chloroform and methanol to obtain 10.1 g of a white solid (a yield of 87.5%).

Synthesis Example 2: Synthesis of Compound Represented by Chemical Formula D-6

[Chemical Formula D-6]

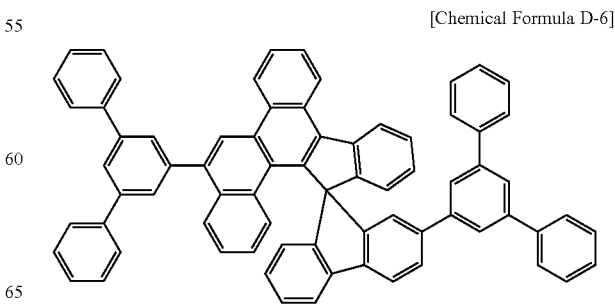

[Reaction Scheme 3]

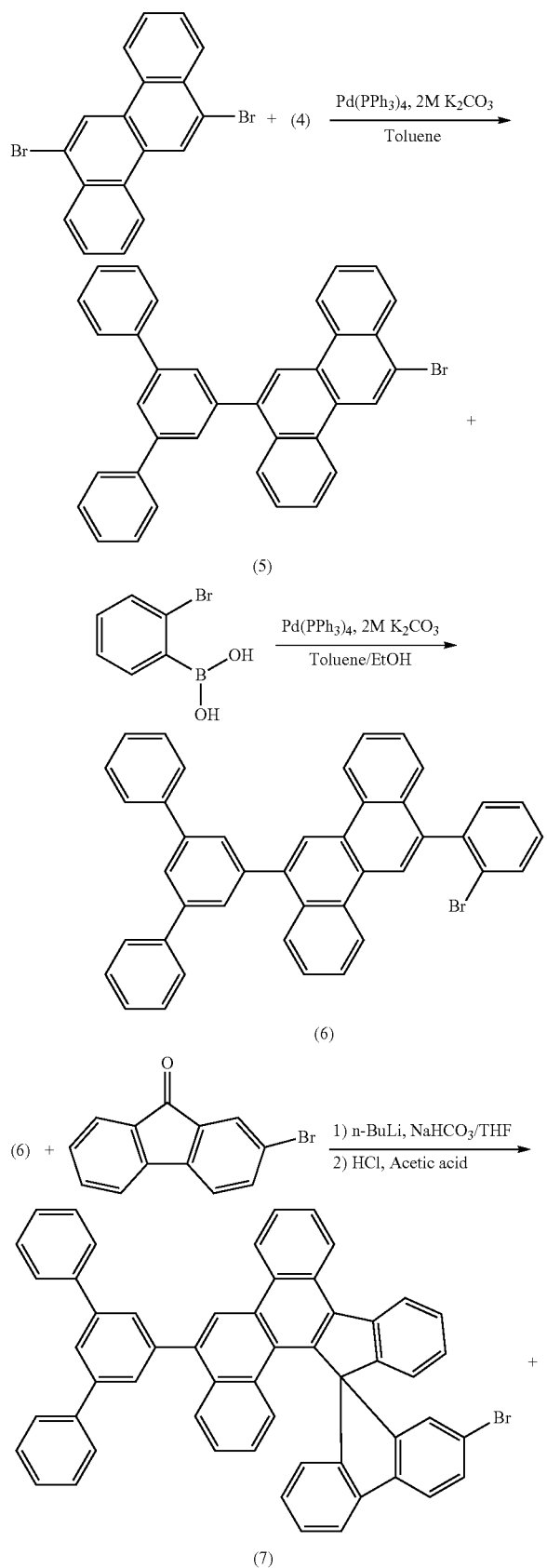

(1) Synthesis of Compound 5

9,12-dibromochrysene (4.0 g, 10.4 mmol), Compound 4 (4.08 g, 11.5 mmol) according to Synthesis Example 1, and Pd(PPh$_3$)$_4$ (0.48 g, 0.42 mmol) were dissolved in 500 mL of an anhydrous toluene solvent under a nitrogen atmosphere. 50 mL of a 2M K$_2$CO$_3$ solution was added thereto. The obtained mixture was heated for 3 hours, while being refluxed under a nitrogen atmosphere. When a reaction was complete, the resultant was extracted with chloroform and distilled water and treated with anhydrous magnesium sulfate. The obtained resulting material was purified by using chloroform: hexane (a volume ratio of 1:7) as an eluting solvent through a silica gel column to obtain 1.28 g of a white solid (a yield of 23.0%).

(2) Synthesis of Compound 6

Compound 5 (5.0 g, 9.4 mmol), 2-bromophenylboronic acid (2.25 g, 11.2 mmol), and Pd(PPh$_3$)$_4$ (0.43 g, 0.37 mmol) were dissolved in 120 mL of an hydrous toluene and 20 mL of an anhydrous ethanol solvent under a nitrogen atmosphere to prepare a mixture. 15 mL of a 2M K$_2$CO$_3$ solution was added thereto. The obtained mixture was heated for 40 minutes while being refluxed under a nitrogen atmosphere. When a reaction was complete, the resultant was extracted with chloroform and distilled water and treated with anhydrous magnesium sulfate. The obtained resulting material was purified by using toluene:hexane (a volume ratio of 1:10) as an eluting solvent through a silica gel column to obtain a white solid of 1.03 g (a yield of 18.1%).

(3) Synthesis of Compound 7

Compound 6 (2.00 g, 3.3 mmol) was dissolved in 40 mL of an anhydrous tetrahydrofuran solvent under a nitrogen atmosphere. 1.96 mL of a 2M normal butyl lithium solution was slowly added thereto at −78° C. 2-bromo-9-fluorenone (1.01 g, 3.9 mmol) dissolved in 25 mL of an anhydrous tetrahydrofuran solvent was added thereto. When a reaction was complete, 50 mL of a 2N sodium bicarbonate aqueous solution was added thereto at room temperature. The obtained mixture was extracted with chloroform and distilled water and treated with anhydrous magnesium sulfate. The solvents were evaporated from the obtained liquid by using an evaporator, and a yellow solid obtained therefrom was dissolved in 200 mL of acetic acid. 20 mL of a HCl aqueous solution was added thereto, and the obtained mixture was heated for one hour while being refluxed. When a reaction was complete, the resultant was extracted with chloroform and distilled water and treated with anhydrous magnesium sulfate. The obtained resulting material was purified by using chloroform:hexane (a volume ratio of 1:3) as an eluting solvent through a silica gel column to obtain of a white solid (a yield of 10.2%).

(4) Synthesis of Compound Represented by Chemical Formula D-6

Compound 7 (0.20 g, 0.26 mmol), Compound 4 (0.11 g, 0.31 mmol), Pd(OAc)$_2$ (0.002 g, 0.01 mmol), and tricyclohexylphosphine (0.006 g, 0.02 mmol) were dissolved in 60 mL of an anhydrous tetrahydrofuran solvent under a nitrogen atmosphere. 6.0 mL of a 20 wt % tetraethylammonium hydroxide aqueous solution was added thereto. The obtained mixture was heated for 3 hours while being refluxed under a nitrogen atmosphere. When a reaction was complete, the resultant was extracted with chloroform and distilled water and treated with anhydrous magnesium sulfate. The obtained resulting material was purified by using chloroform:hexane (a volume ratio of 1:3) as an eluting solvent through a silica gel column to obtain 0.23 g of a white solid (a yield of 95.0%).

[HRMS (FAB+, m/z): cald. For C73H46 922.3600; found, 922.3679].

Evaluation 1: Light Absorption Characteristics

Light absorption characteristics of the compounds according to Comparative Synthesis Example 1 and Synthesis Examples 1 and 2 in a solution and a thin film were evaluated.

The light absorption characteristics in a solution were evaluated by dissolving each compound according to Comparative Synthesis Example 1 and Synthesis Examples 1 and 2 in a tetrahydrofuran solvent at a concentration of $10^{-5}$ M and using a UV-Vis. Spectrometer (Lamda 1050 UV-Vis.-NIR spectrometer, PerkinElmer), and the light absorption characteristics in a thin film were evaluated by vacuum-depositing each compound of Comparative Synthesis Example 1 and Synthesis Examples 1 and 2 on a glass substrate to respectively form a 50 nm-thick thin film and using a UV-Vis. spectrometer (Lamda 1050 UV-Vis.-NIR spectrometer, PerkinElmer). The results are shown in FIGS. 2 and 3.

Figure 2:
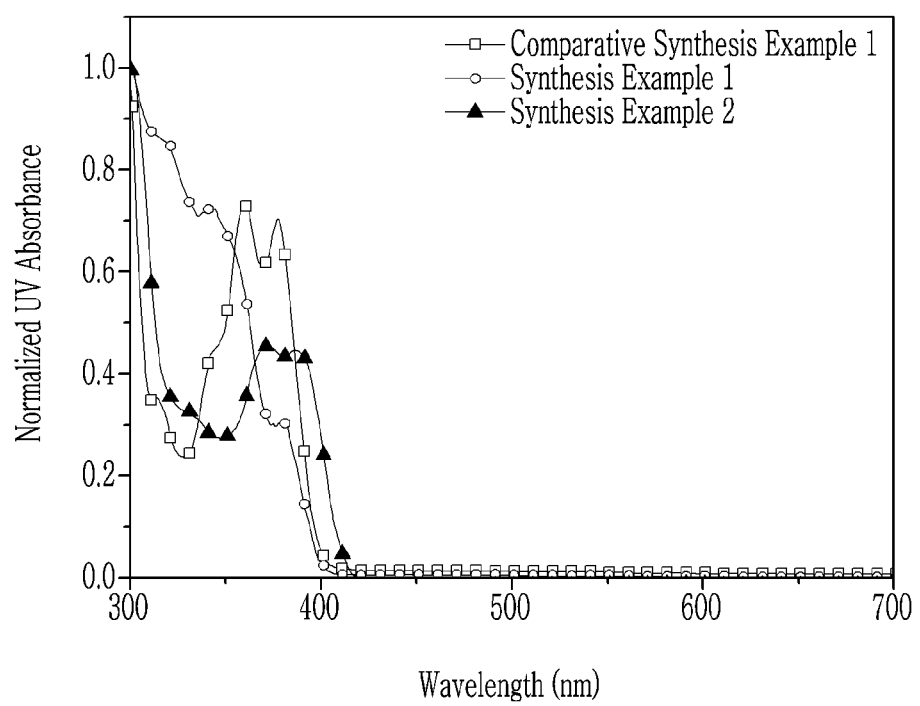
FIG. 2 is a graph showing light absorption characteristics of compounds of Comparative Synthesis Example 1 and Synthesis Examples 1 and 2 in a solution.
Figure 3:
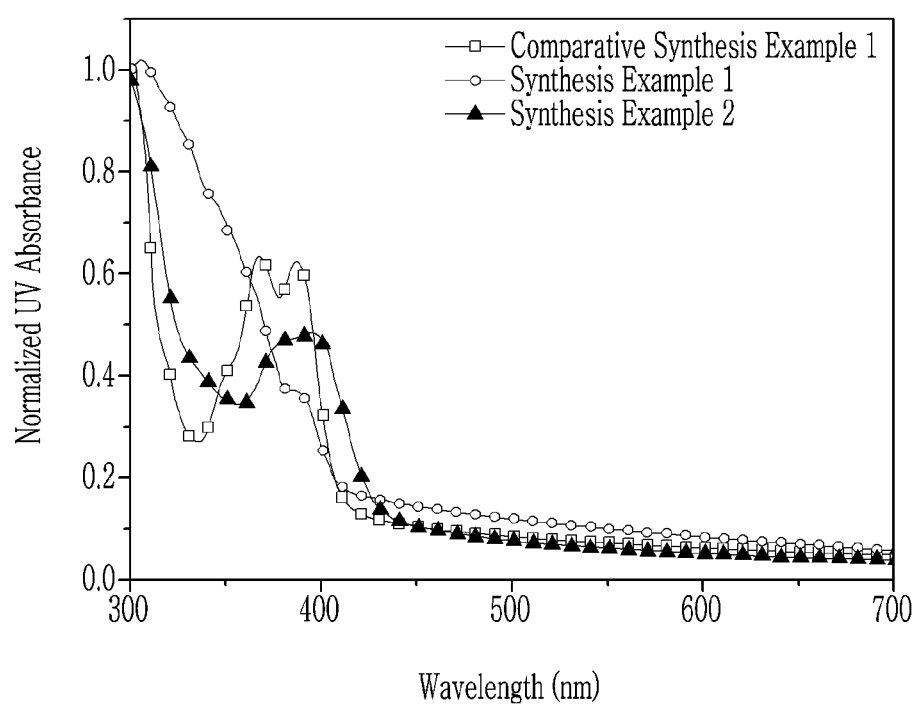
FIG. 3 is a graph showing light absorption characteristics of the compounds of Comparative Synthesis Example 1 and Synthesis Examples 1 and 2 in a thin film.

FIG. 2 is a graph showing light absorption characteristics of the compounds according to Comparative Synthesis Example 1 and Synthesis Examples 1 and 2 in a solution, and FIG. 3 is a graph showing light absorption characteristics of the compounds according to Comparative Synthesis Example 1 and Synthesis Examples 1 and 2 in a thin film.

Referring to FIGS. 2 and 3, the compounds according to Comparative Synthesis Example 1 and Synthesis Examples 1 and 2 all showed sufficient light absorption characteristics. The compounds of Synthesis Examples 1 and 2 showed excellent absorption intensity compared with the compound of Comparative Synthesis Example 1.

Evaluation 2: Light Emitting Characteristics

PL characteristics of the compounds of Comparative Synthesis Example 1 and Synthesis Examples 1 and 2 in a solution and a thin film were evaluated.

The PL characteristics in a solution were evaluated by dissolving each compound of Comparative Synthesis Example 1 and Synthesis Examples 1 and 2 in tetrahydrofuran at a concentration of $10^{-5}$M and using a PL spectrometer (PerkinElmer luminescence spectrometer LS50 (Xenon flash tube)), and the PL characteristics in a thin film were evaluated by respectively vacuum-depositing each compound of Comparative Synthesis Example 1 and Synthesis Examples 1 and 2 on a glass substrate to form each to be a 50 nm-thick thin film and using a PL spectrometer (PerkinElmer luminescence spectrometer LS50 (Xenon flash tube)). The results are shown in FIGS. 4 and 5.

Figure 4:
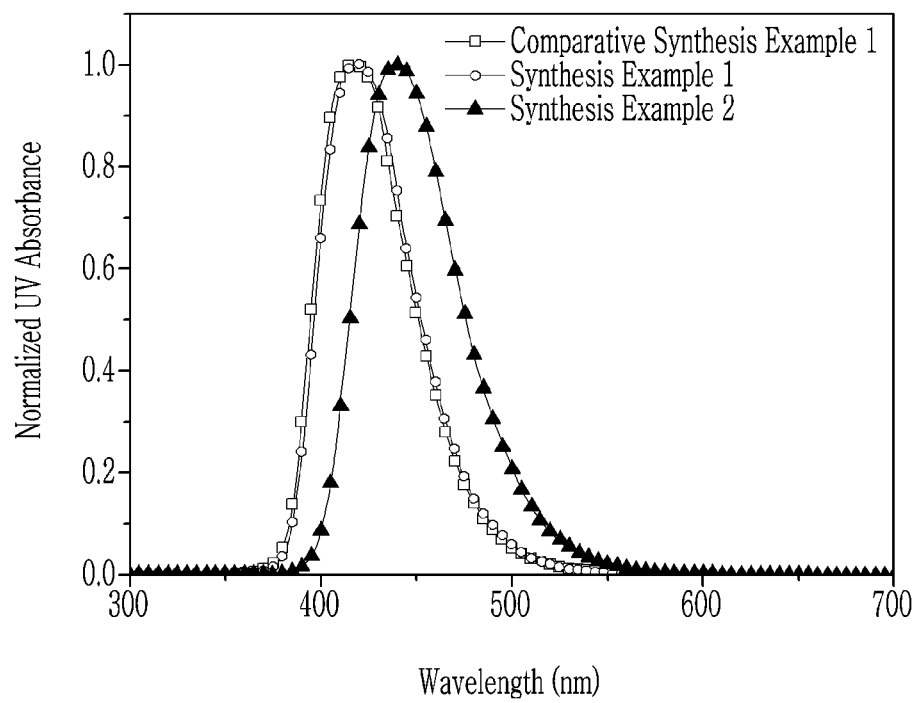
FIG. 4 is a graph showing PL characteristics of the compounds of Comparative Synthesis Example 1 and Synthesis Examples 1 and 2 in a solution.
Figure 5:
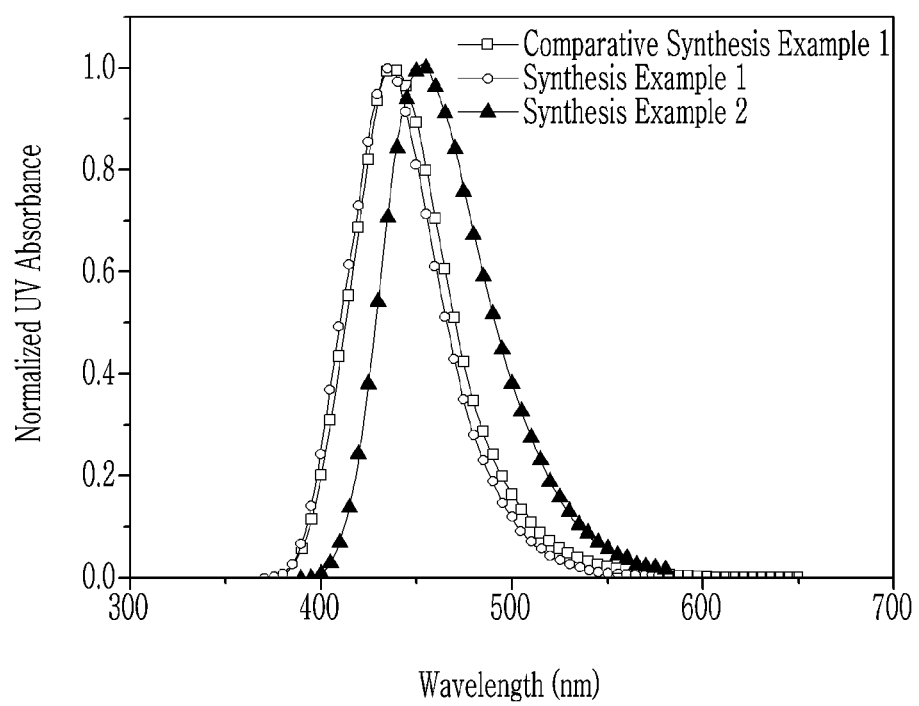
FIG. 5 is a graph showing PL characteristics of the compounds of Comparative Synthesis Example 1 and Synthesis Examples 1 and 2 in a thin film.

FIG. 4 is a graph showing PL characteristics of the compounds of Comparative Synthesis Example 1 and Synthesis Examples 1 and 2 in a solution, and FIG. 5 is a graph showing PL characteristics of the compounds of Comparative Synthesis Example 1 and Synthesis Examples 1 and 2 in a thin film.

Referring to FIGS. 4 and 5, the compounds of Comparative Synthesis Example 1 and Synthesis Examples 1 and 2 turned out to emit light in a blue region. The compound of Synthesis Example 1 showed excellent luminance intensity compared with the compound of Comparative Synthesis Example 1.

Manufacture of Organic Light Emitting Diode

Comparative Example 1

A hole auxiliary layer was formed by sputtering ITO on a glass substrate to be 500 nm thick, and sequentially depositing NPB to be 40 nm thick and TCTA to be 20 nm thick thereon. On the hole auxiliary layer, a 30 nm-thick emission layer was formed by depositing the compound of Comparative Synthesis Example 1. On the emission layer, an electron auxiliary layer was formed by sequentially depositing TPBi (1,3,5-tris(N-phenylbenzimidazole-2-yl)benzene) to be 20 nm thick and LiF to be 1 nm thick. On the electron auxiliary layer, aluminum (Al) was deposited to be 200 nm thick to manufacture an organic light emitting diode.

Example 1

An organic light emitting diode was manufactured according to the same method as Comparative Example 1, except for using the compound of Synthesis Example 1 instead of the compound of Comparative Synthesis Example 1.

Example 2

An organic light emitting diode was manufactured according to the same method as Comparative Example 1, except for using the compound of Synthesis Example 2 instead of the compound of Comparative Synthesis Example 1.

Evaluation 3: Device Evaluation

Electrical characteristics, light emitting characteristics, and color characteristics of the organic light emitting diodes according to Comparative Example 1 and Examples 1 and 2 were evaluated. The results are shown in FIGS. 6 to 9 and Table 1.

Figure 6:
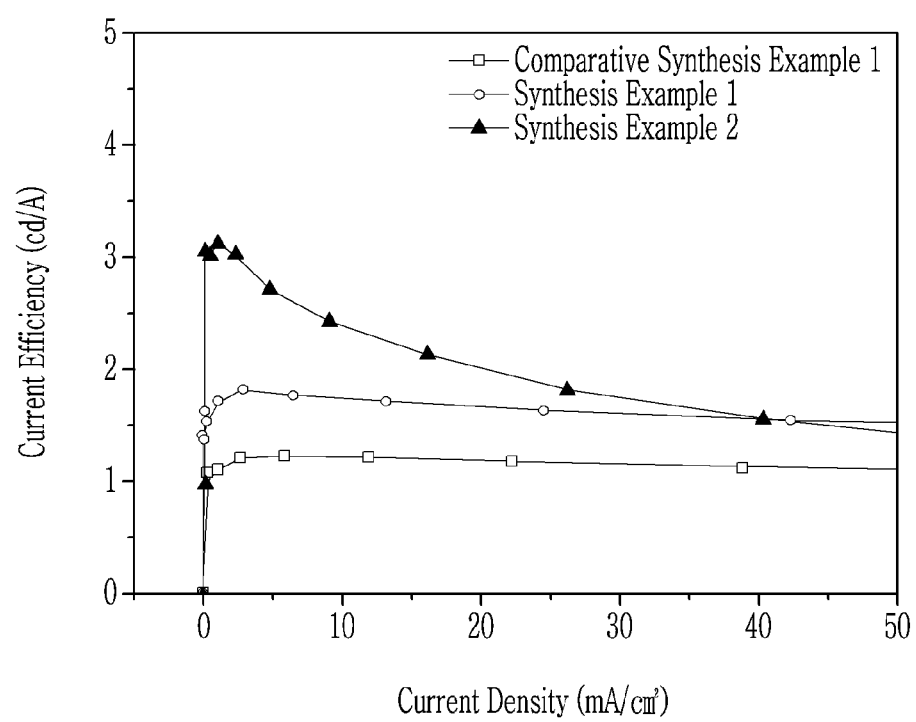
FIG. 6 is a graph showing luminous efficiency of organic light emitting diodes of Comparative Example 1 and Examples 1 and 2.
Figure 7:
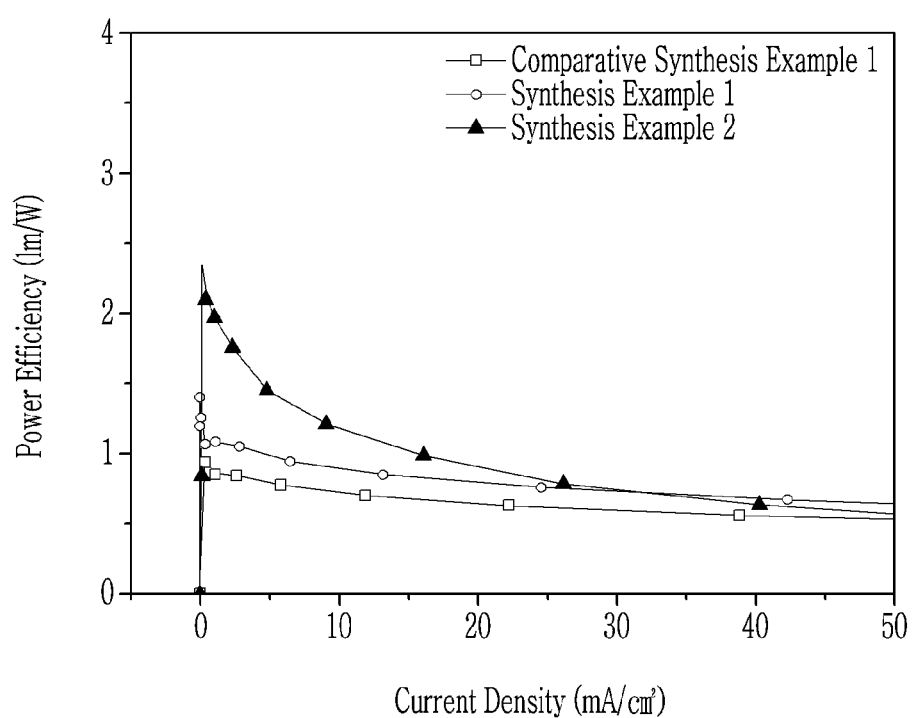
FIG. 7 is a graph showing power efficiency of the organic light emitting diodes of Comparative Example 1 and Examples 1 and 2.
Figure 8:
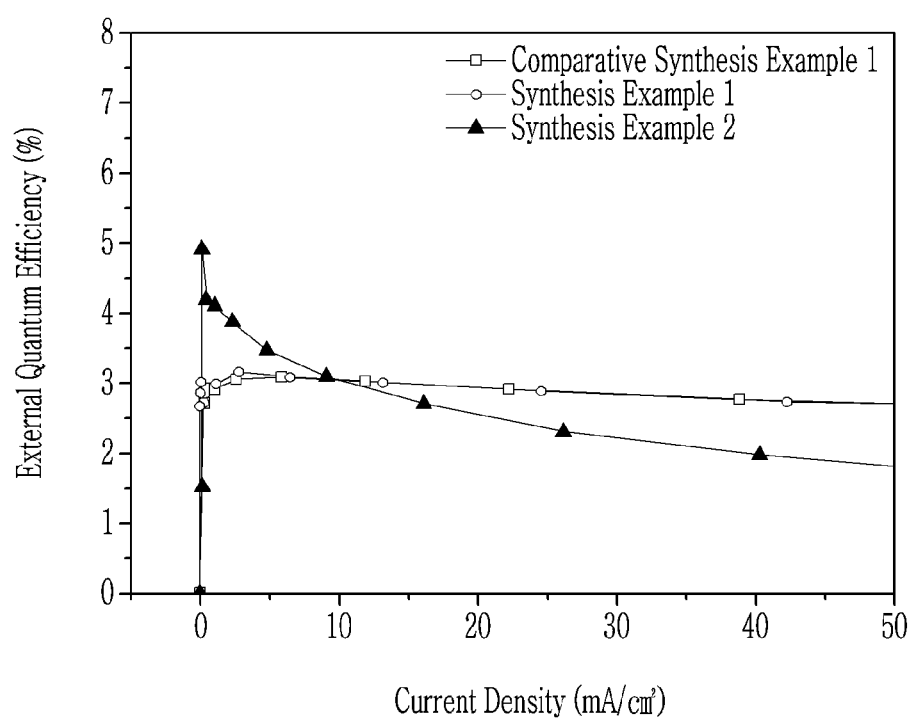
FIG. 8 is a graph showing external quantum efficiency of the organic light emitting diodes of Comparative Example 1 and Examples 1 and 2.
Figure 9:
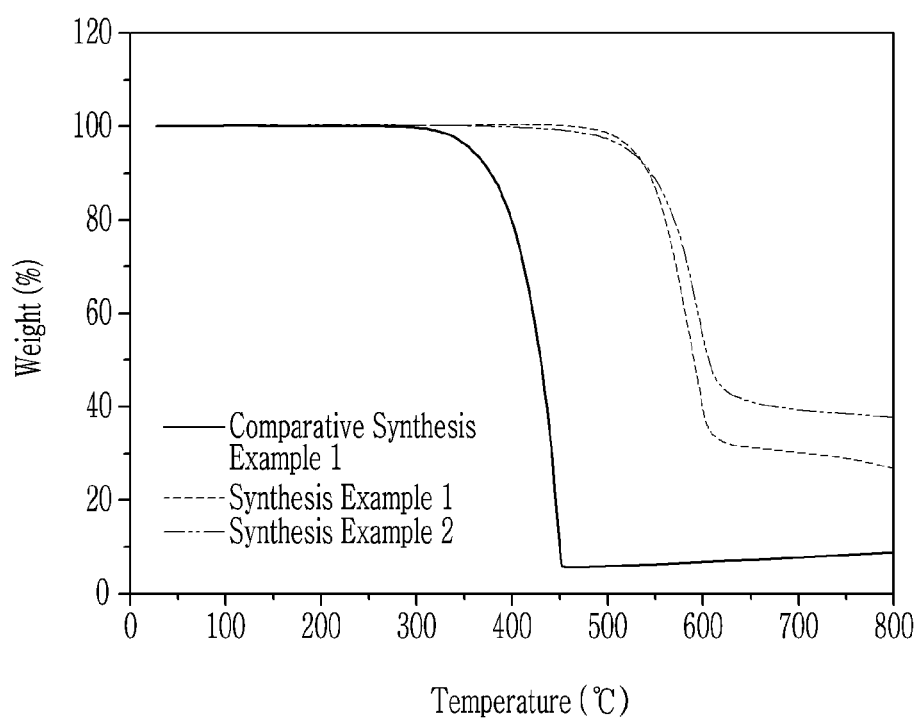
FIG. 9 is a view showing TGA analysis results of the compounds of Comparative Synthesis Example 1 and Synthesis Examples 1 and 2.

FIG. 6 is a graph showing current characteristics and luminance of the organic light emitting diodes according to Comparative Example 1 and Examples 1 and 2, FIG. 7 is a graph showing luminous efficiency of the organic light emitting diodes according to Comparative Example 1 and Examples 1 and 2, FIG. 8 is a graph showing power efficiency of the organic light emitting diodes according to Comparative Example 1 and Examples 1 and 2, and FIG. 9 is a graph showing photoluminescence characteristics of the organic light emitting diode according to Comparative Example 1 and Examples 1 and 2 depending on a wavelength.

Table 1 shows electrical characteristics, light emitting characteristics, and color characteristics of the organic light emitting diodes (current density: 10 mA/cm$^2$) of Comparative Example 1 and Examples 1 and 2.

TABLE 1

|  | Luminous efficiency (cd/A) | Power efficiency (lm/W) | Color coordinates (x, y) | Thin film $EL_{max}$ (nm) | Thin film $PL_{max}$ (nm) |
| --- | --- | --- | --- | --- | --- |
| Comparative Example 1 | 1.21 | 0.70 | (0.153, 0.050) | 435 | 436 |
| Example 1 | 1.68 | 0.88 | (0.154, 0.049) | 435 | 436 |
| Example 2 | 2.39 | 1.19 | (0.148, 0.098) | 453 | 454 |

Referring to Table 1 and FIGS. 6 to 8, the organic light emitting diodes of Examples 1 and 2 respectively showed 39% and 98% increased luminous efficiency and 26% and 70% increased power efficiency compared with the organic light emitting diode of Comparative Example 1.

Evaluation 4: Thermal Stability of Compound

A decomposition temperature $T_d$ was measured by performing TGA (thermogravimetric analysis) of the compounds of Comparative Synthesis Example 1 and Synthesis Examples 1 and 2 under a nitrogen atmosphere with a TGA4000 (PerkinElmer). FIG. 9 is a view showing the TGA analysis results of the compounds of Comparative Synthesis Example 1 and Synthesis Examples 1 and 2.

Referring to FIG. 9, the compound of Comparative Synthesis Example 1 showed a 5% decomposition temperature of 358° C., but the compounds of Synthesis Examples 1 and 2 respectively showed a 5% decomposition temperature of 525° C. and 520° C. Accordingly, the compounds of Synthesis Examples 1 and 2 showed superbly improved thermal stability compared with the compound of Comparative Synthesis Example 1. The compounds having improved thermal stability may realize a stable device, since morphology of the compounds was not easily changed by heat generated while the device is operated. Accordingly, devices respectively including the compounds of Synthesis Examples 1 and 2 may show high efficiency while operated for a long time.

While this invention has been described in connection with what is presently considered to be practical example embodiments, it is to be understood that the invention is not limited to the disclosed embodiments, but, on the contrary, is intended to cover various modifications and equivalent arrangements included within the spirit and scope of the appended claims. Therefore, the aforementioned embodiments should be understood to be exemplary but not limiting the present invention in any way.

DESCRIPTION OF SYMBOLS

110: first electrode
120: second electrode
130: organic layer
100: organic light emitting diode

What is claimed is:

1. A compound for an organic optoelectronic device selected from the group consisting of Chemical Formulae E-7 and E-8:

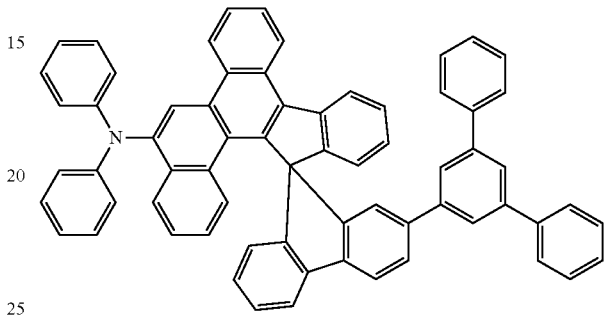

[E-7]

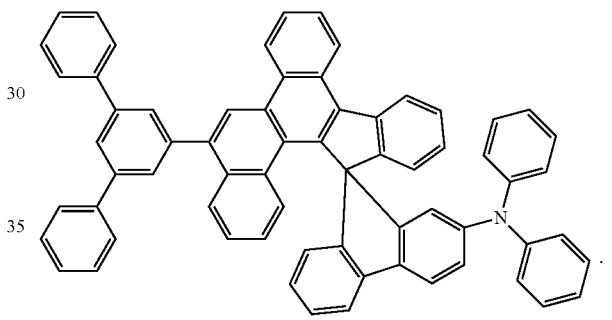

[E-8]

2. An organic optoelectronic device, comprising:
an anode and a cathode facing each other; and
at least one organic layer between the anode and the cathode,
wherein the organic layer includes the compound of claim 1.

3. The organic optoelectronic device of claim 2, wherein the organic layer includes an emission layer, and
the emission layer includes the compound.

* * * * *